United States Patent
Shimizu

(10) Patent No.: US 11,925,442 B2
(45) Date of Patent: Mar. 12, 2024

(54) BLOOD PRESSURE INFORMATION MEASURING SYSTEM, BLOOD PRESSURE INFORMATION MEASURING METHOD, BLOOD PRESSURE INFORMATION MEASURING PROGRAM, BLOOD PRESSURE INFORMATION MEASURING DEVICE, SERVER DEVICE, COMPUTATION METHOD, AND COMPUTATION PROGRAM

(71) Applicant: Arblet Inc., Tokyo (JP)

(72) Inventor: Kosuke Shimizu, Tokyo (JP)

(73) Assignee: Arblet Inc., Tokyo (JP)

( * ) Notice: Subject to any disclaimer, the term of this patent is extended or adjusted under 35 U.S.C. 154(b) by 299 days.

(21) Appl. No.: 16/481,969

(22) PCT Filed: Dec. 26, 2017

(86) PCT No.: PCT/JP2017/046793
§ 371 (c)(1),
(2) Date: Jul. 30, 2019

(87) PCT Pub. No.: WO2018/142821
PCT Pub. Date: Aug. 9, 2018

(65) Prior Publication Data
US 2019/0387977 A1 Dec. 26, 2019

(30) Foreign Application Priority Data
Jan. 31, 2017 (JP) .................. 2017-015597

(51) Int. Cl.
*A61B 5/022* (2006.01)
*A61B 5/00* (2006.01)
(Continued)

(52) U.S. Cl.
CPC .......... *A61B 5/022* (2013.01); *A61B 5/02108* (2013.01); *A61B 5/25* (2021.01); *A61B 5/349* (2021.01); *A61B 5/681* (2013.01)

(58) Field of Classification Search
CPC .......... A61B 5/022; A61B 5/25; A61B 5/349; A61B 5/02108; A61B 5/681; A61B 5/02125
See application file for complete search history.

(56) References Cited

U.S. PATENT DOCUMENTS

2014/0249431 A1*  9/2014  Banet .................... A61B 5/1116
                                                        600/485
2017/0202459 A1*  7/2017  Cao ........................ A61B 5/742
(Continued)

FOREIGN PATENT DOCUMENTS

JP  4-200439 A   7/1992
JP  8-140948 A   6/1996
(Continued)

OTHER PUBLICATIONS

Translation of International Search Report and Written Opinion dated Feb. 6, 2018 in corresponding International application No. PCT/JP2017/046793; 5 pages.
(Continued)

*Primary Examiner* — Yi-Shan Yang
*Assistant Examiner* — Joseph A Tombers
(74) *Attorney, Agent, or Firm* — Maier & Maier, PLLC

(57) ABSTRACT

A system for measuring blood pressure information of a subject, and includes: an electrocardiogram detection unit for detecting an electrocardiogram of the subject; a pulse wave detection unit for detecting pulse waves of the subject; a first computation unit for computing a ventricular systolic phase pulse transit time on the basis of the R wave of the electrocardiogram waveform based on the potential detected (Continued)

by the electrocardiogram detection unit and the P wave of the pulse waveform detected by the pulse wave detection unit, and computing a ventricular diastolic phase pulse transit time on the basis of the T wave of the electrocardiogram waveform and the D wave of the pulse waveform.

21 Claims, 14 Drawing Sheets

(51) Int. Cl.
*A61B 5/021* (2006.01)
*A61B 5/25* (2021.01)
*A61B 5/349* (2021.01)

(56) References Cited

U.S. PATENT DOCUMENTS

2018/0085011 A1* 3/2018 Ma .................. A61B 5/1102
2018/0085040 A1* 3/2018 Ferber .............. A61B 5/7278

FOREIGN PATENT DOCUMENTS

| | | |
|---|---|---|
| JP | 11-299740 A | 11/1999 |
| JP | 2004-81285 A | 3/2004 |
| JP | 2005-532111 A | 10/2005 |
| JP | 2005-537080 A | 12/2005 |
| JP | 2006-280784 A | 10/2006 |
| JP | 2014-108141 A | 6/2014 |
| WO | 2005/112774 A1 | 12/2005 |
| WO | 2006/050059 A2 | 5/2006 |

OTHER PUBLICATIONS

Japanese Office Action dated Jun. 27, 2017 in corresponding application No. 2017-015597; 7 pages.

* cited by examiner

FIG.1
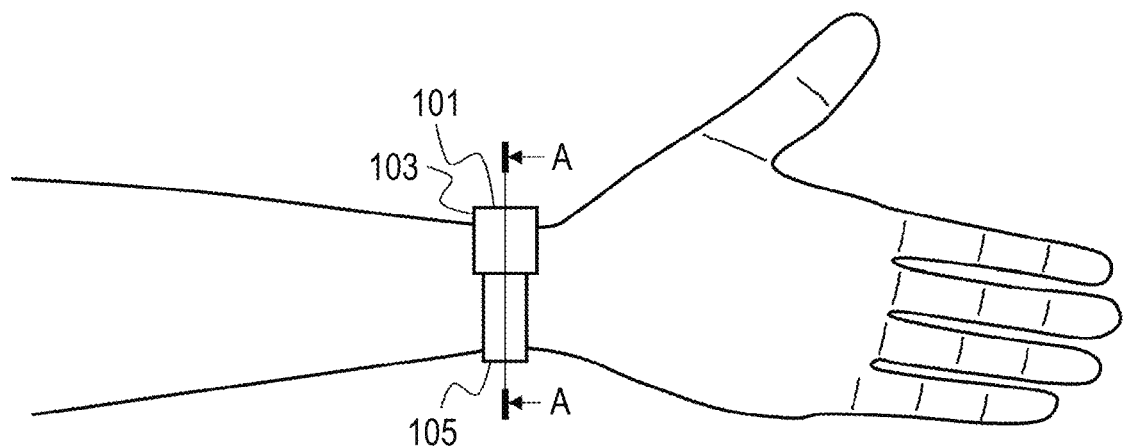
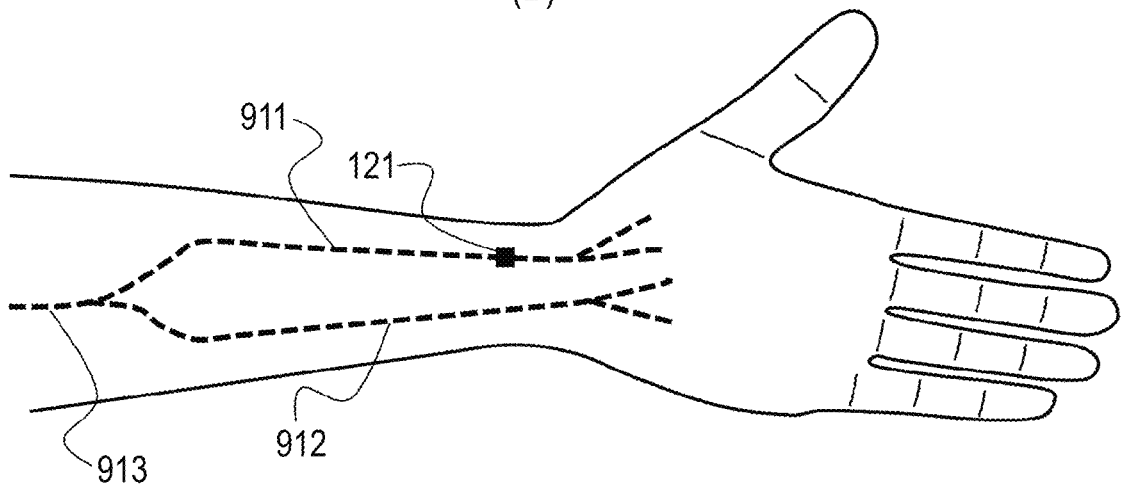
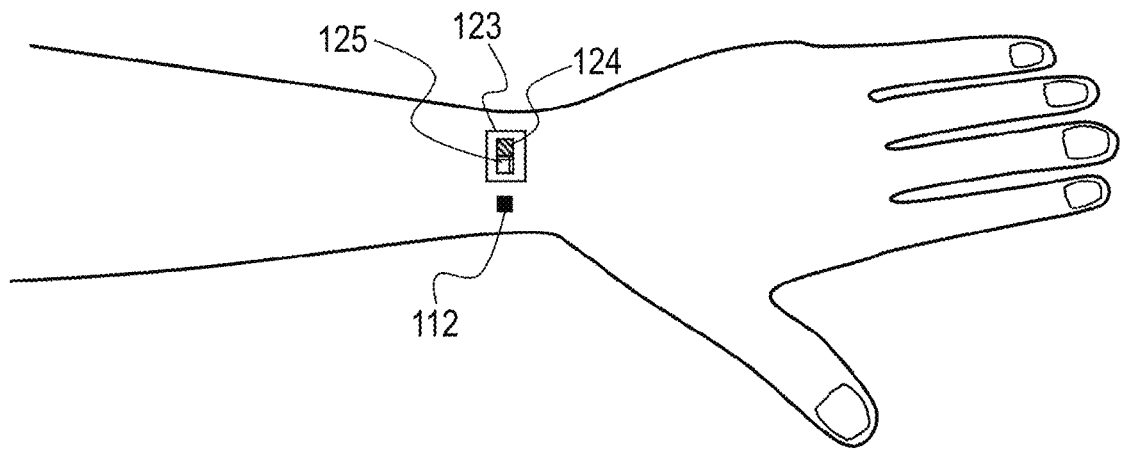

FIG.8
(A)
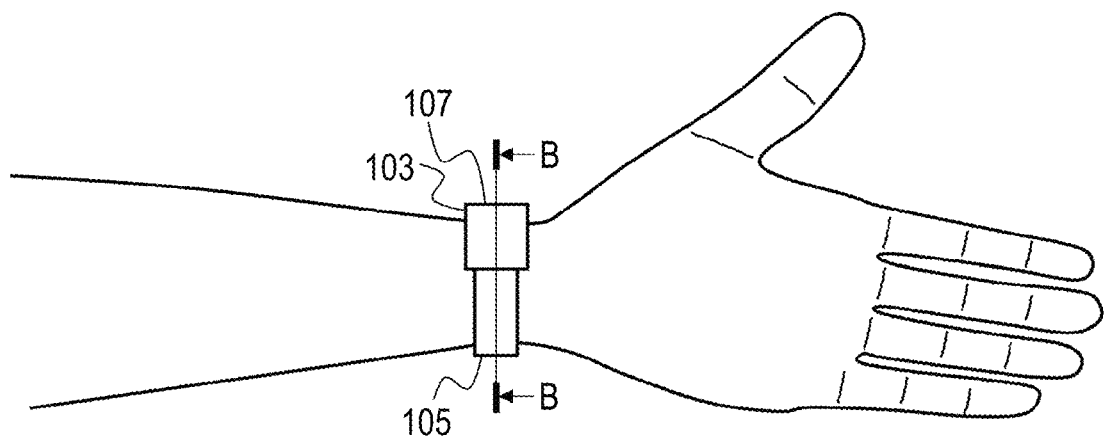
(B)
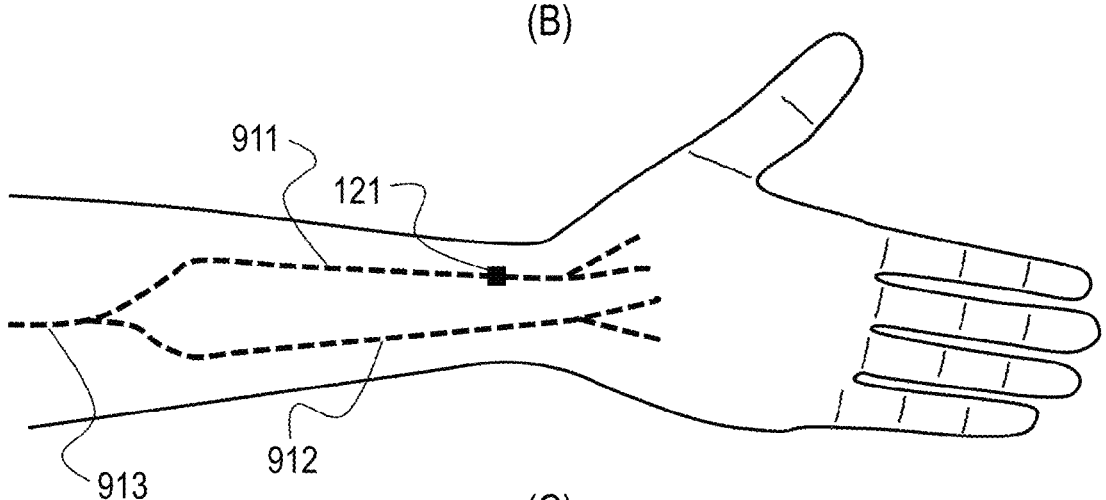
(C)
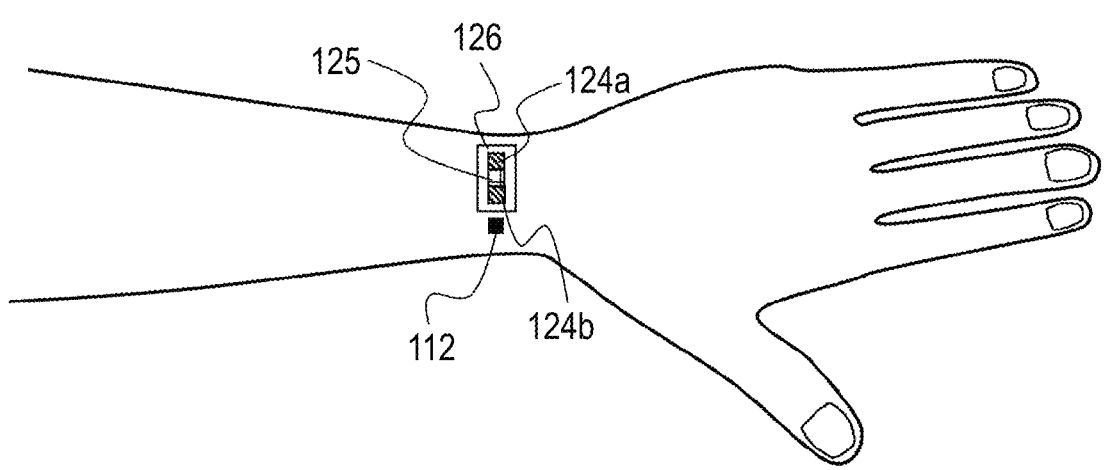

FIG.10
(A)
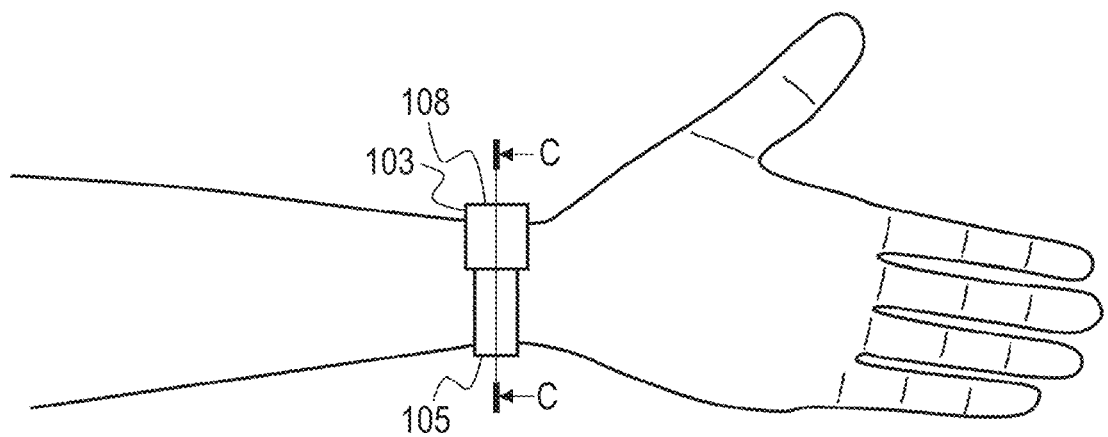
(B)
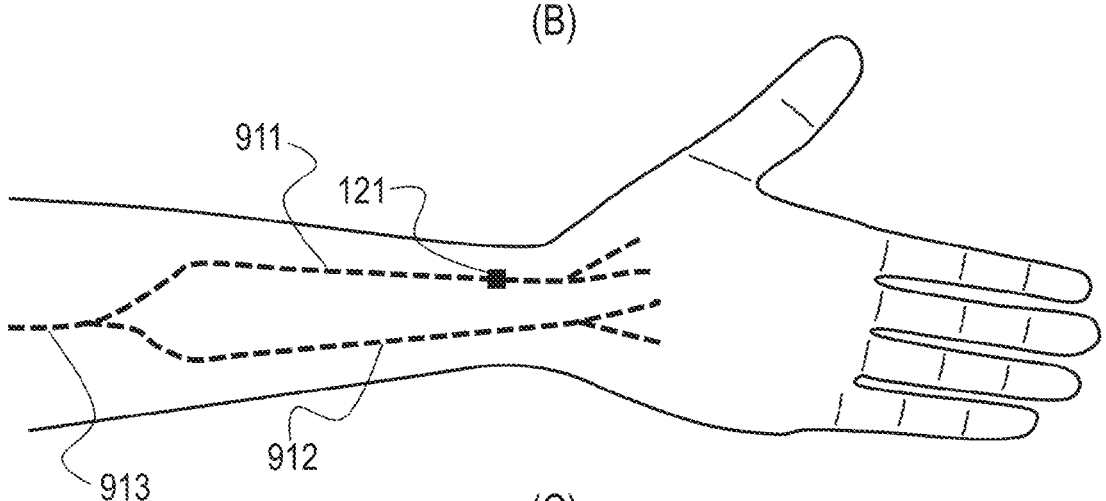
(C)
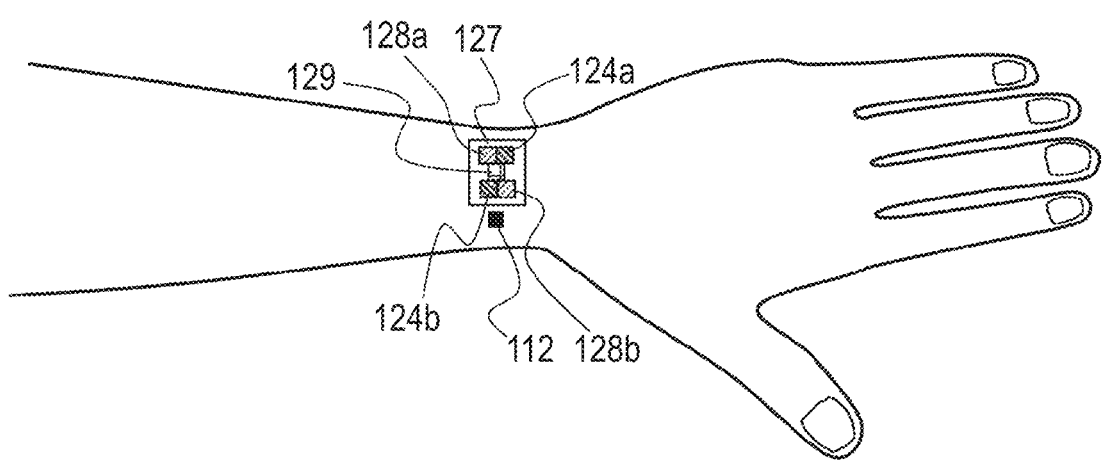

FIG.12
(A)
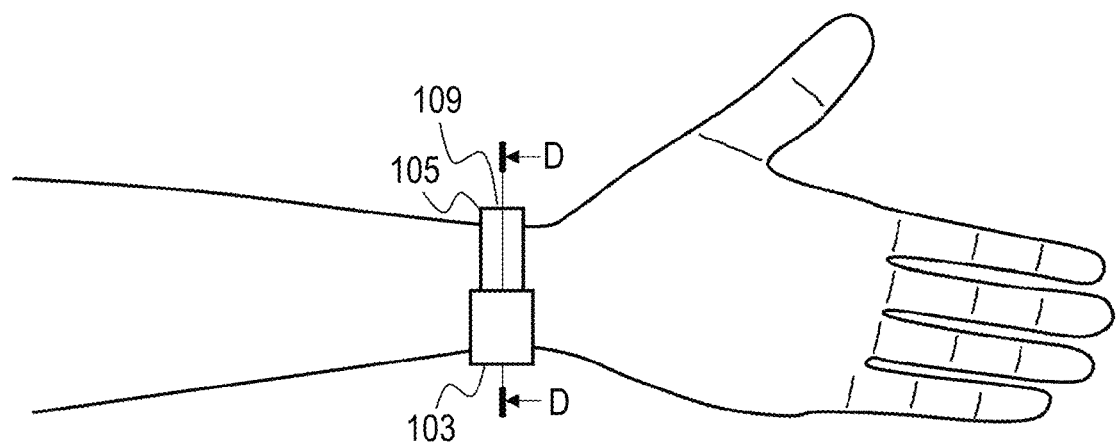
(B)
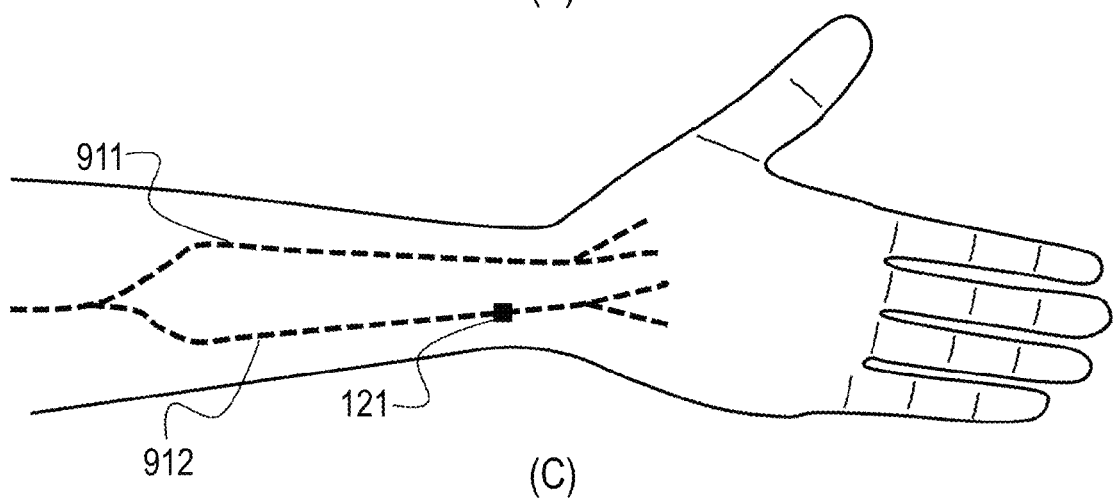
(C)
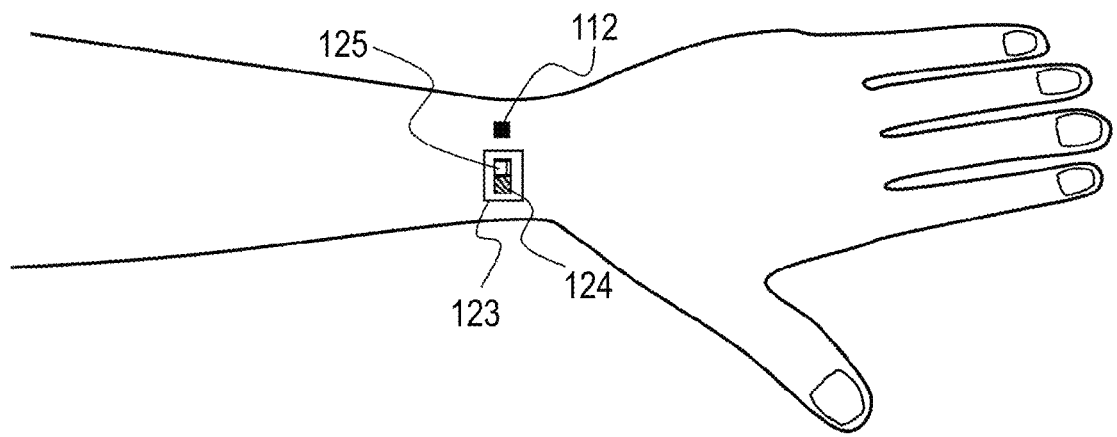

BLOOD PRESSURE INFORMATION MEASURING SYSTEM, BLOOD PRESSURE INFORMATION MEASURING METHOD, BLOOD PRESSURE INFORMATION MEASURING PROGRAM, BLOOD PRESSURE INFORMATION MEASURING DEVICE, SERVER DEVICE, COMPUTATION METHOD, AND COMPUTATION PROGRAM

FIELD

The present invention relates to a blood pressure information measuring system, a blood pressure information measuring method, a blood pressure information measuring program, a blood pressure information measuring device, a server device, a computation method, and a computation program, for measuring blood pressure information of a subject.

BACKGROUND

It is effective for health management to measure blood pressure continuously, to detect diseases early from change of the blood pressure and detect changes in medical condition. Therefore, there has been proposed a continuous blood pressure measuring device or a method for continuously measuring the blood pressure without pressurizing an arm or the like with a cuff or the like.

For example, Patent Literature 1 proposes a portable blood pressure measuring device including an electrocardiogram detection unit mounted on one arm and having one electrode in contact with a surface of a living body, and a plethysmogram detection unit having a photoelectric sensor in contact with the surface of the living body, wherein the electrocardiogram detection unit detects a cardiac potential induced by electrodes as a potential with respect to a ground of the electrocardiogram detection unit, to measure an electrocardiogram and a plethysmogram to determine a transfer time of the plethysmogram and to compute the maximum value and the minimum value of the blood pressure.

Further, in a blood pressure measuring method without using the cuff or the like, a diastolic blood pressure is generally computed using a conversion formula from a systolic blood pressure, which is computed based on a ventricular systolic phase pulse transit time calculated from an R wave of an electrocardiogram waveform and a P wave of a pulse waveform, which are easy to detect.

Patent Literature 1: JP-A-2004-081285

SUMMARY

However, more accurate change information on the systolic blood pressure and the diastolic blood pressure is required in order to improve early detection of diseases and detection accuracy of medical condition changes.

Therefore, an object of the present invention is to provide the blood pressure information measuring system which is always worn by the subject and capable of measuring more accurate blood pressure information on the systolic blood pressure and the diastolic blood pressure, the blood pressure information measuring method, the blood pressure information measuring program, the blood pressure information measuring device, the server device, the computation method and the computation program.

In order to solve the above problems, a blood pressure information measuring system of the present invention is a system for measuring blood pressure information of a subject. The system includes: an electrocardiogram detection unit for detecting an electrocardiogram of the subject; a pulse wave detection unit for detecting a pulse wave of the subject; a first computation unit for computing a ventricular systolic phase pulse transit time from an R wave of an electrocardiogram waveform based on a potential detected by the electrocardiogram detection unit and a P wave of a pulse waveform detected by the pulse wave detection unit, and computing a ventricular diastolic phase pulse transit time from a T wave of the electrocardiogram waveform and a D wave of the pulse waveform; and a second computation unit for computing information on a systolic blood pressure of the subject and information on a diastolic blood pressure of the subject from the ventricular systolic phase pulse transit time and the ventricular diastolic phase pulse transit time computed by the first computation unit.

A blood pressure information measuring method of the present invention is a method for measuring blood pressure information of a subject. The method includes the following steps: an electrocardiogram detection step of detecting an electrocardiogram of the subject by an electrocardiogram detection unit; a pulse wave detection step of detecting a pulse wave of the subject by the pulse wave detection unit; a first computation step of computing a ventricular systolic phase pulse transit time from an R wave of an electrocardiogram waveform based on a potential detected in the electrocardiogram detection step by a first computation unit and a P wave of a pulse waveform detected in the pulse wave detection step, and a ventricular diastolic phase pulse transit time from a T wave of the electrocardiogram waveform and a D wave of the pulse waveform; and a second computation step of computing information on a systolic blood pressure of the subject and information on a diastolic blood pressure of the subject from the ventricular systolic phase pulse transit time and the ventricular diastolic phase pulse transit time which are computed in the first computation step by a second computation unit.

A blood pressure information measuring program of the present invention is a program for measuring blood pressure information of a subject. The program causes a computer to perform the following steps: an electrocardiogram detection step of detecting an electrocardiogram of the subject by an electrocardiogram detection unit; a pulse wave detection step of detecting a pulse wave of the subject by the pulse wave detection unit; a first computation step of computing a ventricular systolic phase pulse transit time from an R wave of an electrocardiogram waveform based on a potential detected in the electrocardiogram detection step by a first computation unit and a P wave of a pulse waveform detected in the pulse wave detection step, and a ventricular diastolic phase pulse transit time from a T wave of the electrocardiogram waveform and a D wave of the pulse waveform; and a second computation step of computing information on a systolic blood pressure of the subject and information on a diastolic blood pressure of the subject from the ventricular systolic phase pulse transit time and the ventricular diastolic phase pulse transit time which are computed in the first computation step by a second computation unit.

A blood pressure information measuring device of the present invention is a device for measuring blood pressure information of a subject. The device includes: an electrocardiogram detection unit for detecting an electrocardiogram of the subject; a pulse wave detection unit for detecting a pulse wave of the subject; a first computation unit for computing a ventricular systolic phase pulse transit time from an R wave of an electrocardiogram waveform based on a potential detected by the electrocardiogram detection unit and a P wave of a pulse waveform detected by the pulse wave detection unit, and computing a ventricular diastolic phase pulse transit time from a T wave of the electrocardiogram waveform and a D wave of the pulse waveform; and a second computation unit for computing information on a systolic blood pressure of the subject and information on a diastolic blood pressure of the subject from the ventricular systolic phase pulse transit time and the ventricular diastolic phase pulse transit time computed by the first computation unit.

A server device of the present invention is a server device, which can be connected to a blood pressure information measuring device having an electrocardiogram detection unit for detecting an electrocardiogram of a subject and a pulse wave detection unit for detecting a pulse wave of the subject, and computes blood pressure information of the subject. The server device includes a computation unit for computing information on a systolic blood pressure of the subject and information on a diastolic blood pressure of the subject, from a ventricular systolic phase pulse transit time computed from an R wave of an electrocardiogram waveform based on a potential detected by the electrocardiogram detection unit and a P wave of a pulse waveform detected by the pulse wave detection unit, and a ventricular diastolic phase pulse transit time computed from a T wave of the electrocardiogram waveform and a D wave of the pulse waveform.

A server device of the present invention is a server device, which can be connected to a blood pressure information measuring device having an electrocardiogram detection unit for detecting an electrocardiogram of a subject and a pulse wave detection unit for detecting a pulse wave of the subject, and computes blood pressure information of the subject. The server device includes: a first computation unit for computing a ventricular systolic phase pulse transit time from an R wave of an electrocardiogram waveform based on a potential detected by the electrocardiogram detection unit and a P wave of a pulse waveform detected by the pulse wave detection unit, and computing a ventricular diastolic phase pulse transit time from a T wave of the electrocardiogram waveform and a D wave of the pulse waveform; and a second computation unit for computing information on a systolic blood pressure of the subject and information on a diastolic blood pressure of the subject from the ventricular systolic phase pulse transit time and the ventricular diastolic phase pulse transit time computed by the first computation unit.

A computation method of the present invention is a computation method for computing blood pressure information of a subject by a server device, which can be connected to a blood pressure information measuring device having an electrocardiogram detection unit for detecting an electrocardiogram of the subject and a pulse wave detection unit for detecting a pulse wave of the subject. A computation unit computes information on a systolic blood pressure of the subject and information on a diastolic blood pressure of the subject, from a ventricular systolic phase pulse transit time computed from an R wave of an electrocardiogram waveform based on a potential detected by the electrocardiogram detection unit and a P wave of a pulse waveform detected by the pulse wave detection unit, and a ventricular diastolic phase pulse transit time computed from a T wave of the electrocardiogram waveform and a D wave of the pulse waveform.

A computation program of the present invention is a computation program for computing blood pressure information of a subject by a computer, which can be connected to a blood pressure information measuring device having an electrocardiogram detection unit for detecting an electrocardiogram of the subject and a pulse wave detection unit for detecting a pulse wave of the subject. A computation unit causes the computer to compute information on a systolic blood pressure of the subject and information on a diastolic blood pressure of the subject, from a ventricular systolic phase pulse transit time computed from an R wave of an electrocardiogram waveform based on a potential detected by the electrocardiogram detection unit and a P wave of a pulse waveform detected by the pulse wave detection unit, and a ventricular diastolic phase pulse transit time computed from a T wave of the electrocardiogram waveform and a D wave of the pulse waveform.

According to the above-described blood pressure information measuring system, blood pressure information measuring method, blood pressure information measuring program, blood pressure information measuring device, server device, computation method, and computation program, it is possible for the subject to always wear the system and to measure more accurate blood pressure information on the systolic blood pressure and the diastolic blood pressure.

BRIEF DESCRIPTION OF THE DRAWINGS

FIG. 1A is view for explaining a left arm of a subject, a blood pressure information measuring device, an electrode of a measurement site, and the like according to a first embodiment.

FIG. 1B is view for explaining a left arm of a subject, a blood pressure information measuring device, an electrode of a measurement site, and the like according to a first embodiment.

FIG. 1C is view for explaining a left arm of a subject, a blood pressure information measuring device, an electrode of a measurement site, and the like according to a first embodiment.

FIG. 8A is view for explaining the left arm of the subject, the blood pressure information measuring device, the electrode of the measurement site, and the like according to a third embodiment.

FIG. 8B is view for explaining the left arm of the subject, the blood pressure information measuring device, the electrode of the measurement site, and the like according to a third embodiment.

FIG. 8C is view for explaining the left arm of the subject, the blood pressure information measuring device, the electrode of the measurement site, and the like according to a third embodiment.

FIG. 10A is view for explaining the left arm of the subject, the blood pressure information measuring device, the electrode of the measurement site, and the like according to a fourth embodiment.

FIG. 10B is view for explaining the left arm of the subject, the blood pressure information measuring device, the electrode of the measurement site, and the like according to a fourth embodiment.

FIG. 10C is view for explaining the left arm of the subject, the blood pressure information measuring device, the electrode of the measurement site, and the like according to a fourth embodiment.

FIG. 12A is view for explaining the left arm of the subject, the blood pressure information measuring device, the electrode of the measurement site, and the like according to a fifth embodiment.

FIG. 12B is view for explaining the left arm of the subject, the blood pressure information measuring device, the electrode of the measurement site, and the like according to a fifth embodiment.

FIG. 12C is view for explaining the left arm of the subject, the blood pressure information measuring device, the electrode of the measurement site, and the like according to a fifth embodiment.

DETAILED DESCRIPTION

The present embodiment will be described below. Note that embodiments described below do not unduly limit contents of the present invention described in claims. Further, all of components described in the present embodiment are not necessarily essential components of the present invention.

First Embodiment

<Configuration>

Figure 2:
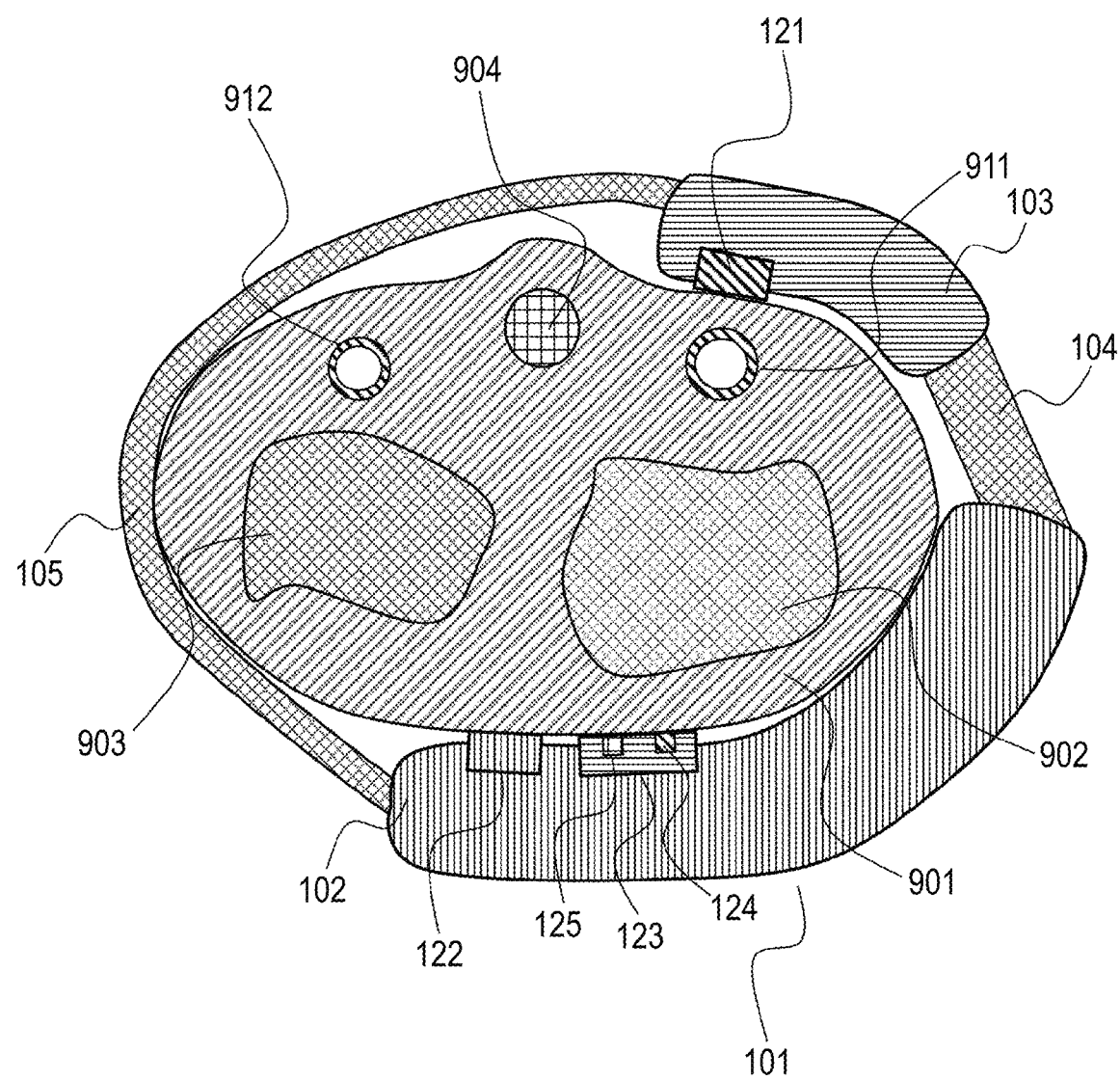
FIG. 2 is a view for explaining the left arm of the subject wearing the blood pressure information measuring device according to the first embodiment, and a cross-section taken along a line A-A in FIG. 1A of the blood pressure information measuring device.

An arm which is a measurement site of a subject and a blood pressure information measuring device 101 of a blood pressure information measuring system 1 in a first embodiment will be described using FIGS. 1A to 1C and 2. FIG. 1A is a state in which the blood pressure information measuring device 101 is mounted on a left arm of the subject. FIG. 1B is a perspective view of a radial artery and an ulnar artery in the left arm of the subject, and shows a positional relationship between the radial artery and an electrode of the blood pressure information measuring device. FIG. 1C is a view showing a positional relationship among the arm of the subject, the electrode of the blood pressure information measuring device 101, and an optical sensor. FIG. 2 shows a cross-section taken along a line A-A in FIG. 1A.

As shown in FIG. 1A and FIG. 2, the blood pressure information measuring device 101 includes a main unit 102 and a subunit 103, and one ends of the main unit 102 and the subunit 103 are connected to each other by a link band 104 made of rubber with electrical wiring disposed therein. Further, the other ends of the main unit 102 and the subunit 103 are connected to each other by a rubber support band 105 for fixing the blood pressure information measuring device 101 to a wrist 901. With such a configuration, when the link band 104 is deformed, the main unit 102 and the subunit 103 can be pulled together by rubber elasticity of the support band 105. Therefore, the subject can bring the main unit 102 and the subunit 103 into close contact with the wrist 901 of the subject regardless of thickness of the wrist 901. Note that the main unit 102 and the subunit 103 may be configured to communicate wirelessly without being connected by the electrical wiring. Further, the support band 105 may be matched to a diameter of the wrist by means of a buckle and a hole as two bands like a watch belt.

The main unit 102 is configured to include a second electrode 122, an optical sensor module 123, a measuring device control unit and the like described below. The main unit 102 includes a measuring device control unit 113 and the like described below. The subunit 103 is provided with a first electrode 121.

As shown in FIG. 1B and FIG. 2, a radial artery 911 and an ulnar artery 912 pass through the arm of the subject. As shown in FIG. 2, the wrist 901 has a radius 902 and an ulna 903 passing therethrough, the radial artery 911 passes between the radius 902 and a skin on a surface of the wrist, and the ulnar artery 912 passes between the ulna 903 and the skin on the surface of the wrist. The radial artery 911 and the ulnar artery 912 are branched from a brachial artery 913 in an upper arm. A tendon 904 is between the radial artery 911 and the ulnar artery 912. The tendon 904 may protrude to raise the skin on the surface of the wrist by movement of the wrist 901. Therefore, as shown in FIG. 2, the main unit 102 and the subunit 103 of the blood pressure information measuring device 101 do not easily touch the skin near the tendon 904, which can make it difficult for the subject to feel discomfort in wearing. In addition, a thickness of the subunit 103 has an effect of making it difficult for the support band 104 to touch the skin near the tendon 904.

The first electrode 121 shown in FIG. 1B and FIG. 2 is disposed near the radial artery on a back side of hand of the wrist 901, and detects a potential associated with an electrocardiogram from the radial artery. The second electrode 122 shown in FIG. 1C and FIG. 2 is disposed on a palm side of the wrist 901, and detects a living body reference potential. With such a configuration, by measuring the potential detected by the first electrode 121 with the second electrode 122 as the reference potential as time passes, it is possible to obtain the electrocardiogram and measure an electrocardiogram waveform. In addition, since the second electrode 122 can suppress variation of measured reference potential, it is possible to improve detection accuracy of the electrocardiogram waveform accompanied by a minute change of a T wave and the like described below, and to accurately measure a change in ventricular diastolic phase pulse transit time PTT_DIA (Pulse Transit Time_Diastolic) described below.

As shown in FIG. 1C and FIG. 2, the optical sensor module 123 is configured to include a light emitter 124 and a light receiver 125. The light emitter 124 is a light emitting LED having a center wavelength of 660 nm, and the light receiver 125 is formed of a photodiode capable of receiving light emitted from the light emitter 124 formed of the light emitting LED. The light emitted from the light emitter 124 to the wrist is reflected inside the wrist and received by the light receiver 125. Temporal change in intensity of the light received by the light receiver 125 makes it possible to measure a pulse waveform based on a change in volume of blood vessel caused by heartbeat of the subject. The pulse waveform which can be detected in this manner is a photoplethysmogram waveform. The optical sensor module 123 is disposed on the palm side of the wrist 901, and is disposed at a position facing the first electrode 121 via the wrist 901. This makes it possible to separate a measurement site of the electrocardiogram waveform to be measured by the first electrode 121 and a measurement site of the photoplethysmogram waveform to be measured by the optical sensor module 123. Thus, it is possible to lengthen a ventricular systolic phase pulse transit time PTT_SYS (Pulse Transit Time_Systolic) described below and the ventricular diastolic phase pulse transit time PTT_DIA, thereby improving reliability of measurement.

Figure 3:
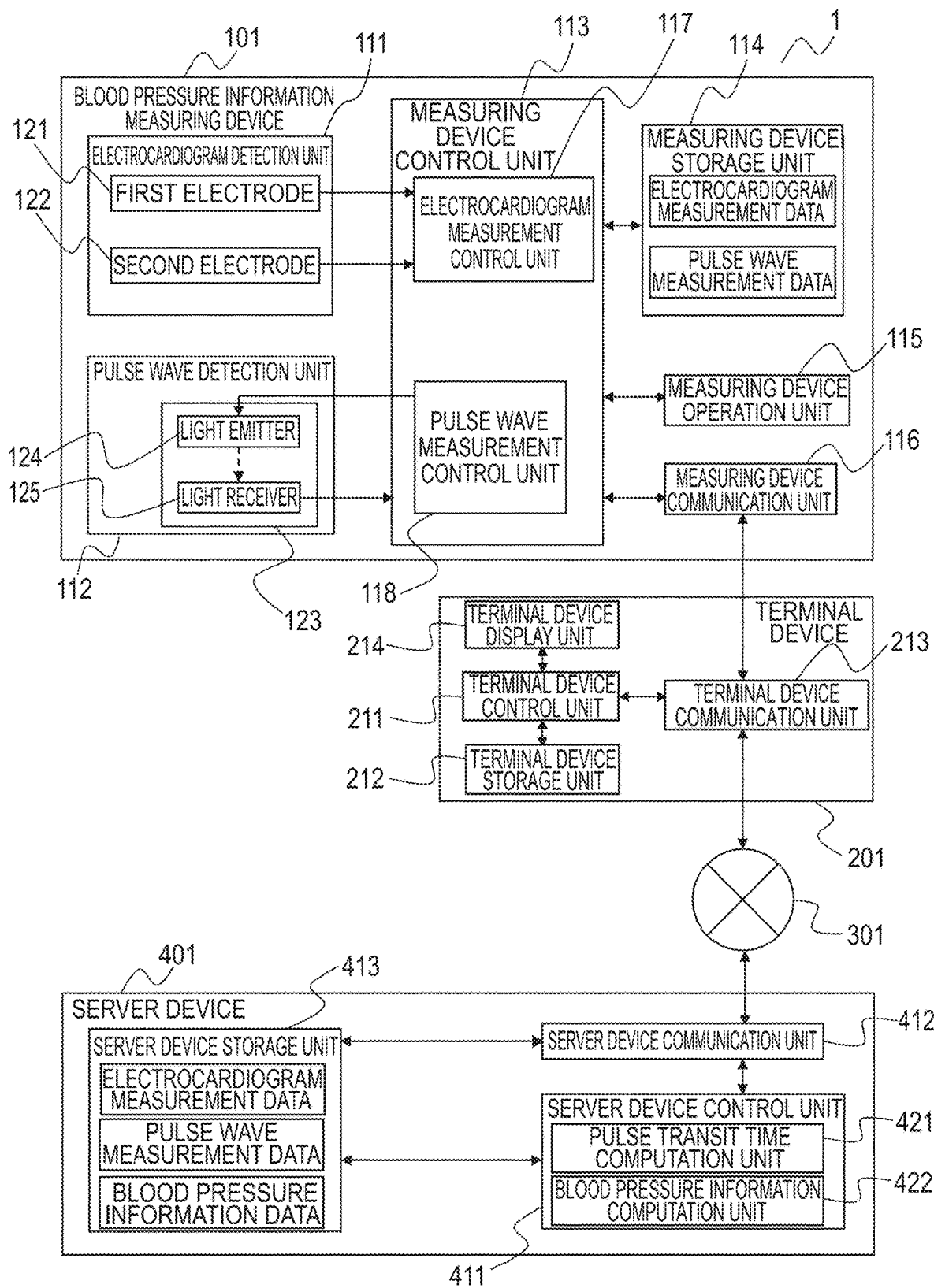
FIG. 3 is a schematic block diagram showing a configuration of a blood pressure information measuring system according to the first embodiment.

Next, the configuration and outline of the blood pressure information measuring system 1 including a server device 401 for computing blood pressure information of the subject based on information from the blood pressure information measuring device 101 in the first embodiment will be described with reference to FIG. 3. FIG. 3 is a block diagram of the blood pressure information measuring system 1 of the present embodiment.

As shown in FIG. 3, the blood pressure information measuring system 1 of the present embodiment is constituted by the blood pressure information measuring device 101, a terminal device 201 and the server device 401. The terminal device 201 and the server device 401 are configured to be connectable to a network 301 such as the Internet or LAN.

The blood pressure information measuring device 101 is configured to include an electrocardiogram detection unit 111, a pulse wave detection unit 112, a measuring device control unit 113, a measuring device storage unit 114, a measuring device operation unit 115, and a measuring device communication unit 116.

The electrocardiogram detection unit 111 is configured to include the first electrode 121 for detecting the electrocardiogram of the radial artery and the second electrode 122 for measuring the living body reference potential.

The pulse wave detection unit 112 is configured to include the optical sensor module 123. The optical sensor module 123 includes the light emitter 124 and the light receiver 125.

The measuring device control unit 113 is configured to include an electrocardiogram measurement control unit 117 and a pulse wave measurement control unit 118. The electrocardiogram measurement control unit 117 detects a difference between detection potentials from the first electrode 121 and the second electrode 122, and adds time information to form the electrocardiogram waveform. The pulse wave measurement control unit 118 performs light emission control of the light emitter 124 of the pulse wave detection unit 112, and receives a detection signal from the light receiver 125.

The measuring device storage unit 114 stores electrocardiogram measurement data received by the electrocardiogram measurement control unit 117, and stores pulse wave measurement data received by the pulse wave measurement control unit 118. The electrocardiogram measurement data is information on the electrocardiogram waveform in which electrocardiogram information detected by the first electrode is continuously arranged, and is added with measurement time information and the like of the electrocardiogram waveform. The pulse wave measurement data is information on the photoplethysmogram waveform in which a pulse wave detected by the optical sensor module 123 is continuously arranged, and is added with the measurement time information and the like of the photoplethysmogram waveform. Although the electrocardiogram measurement data and the pulse wave measurement data are transmitted to the terminal device 201 via the measuring device communication unit 116 described below, they can be temporarily stored for cases such as when a transmission frequency may be reduced to save power or the like, or when communication connection with the terminal device 201 is disconnected.

The measuring device operation unit 115 is an operation unit for the subject or the like to perform an operation of power of the blood pressure information measuring device 101 and an operation such as measurement start and end.

The measuring device communication unit 116 is a communication interface for communicating the blood pressure information measuring device 101 with external devices such as the terminal device 201. The measuring device communication unit 116 transmits, for example, the electrocardiogram measurement data received by the electrocardiogram measurement control unit 117, the pulse wave measurement data received by the pulse wave measurement control unit 118, or the electrocardiogram measurement data or the pulse wave measurement data stored in the measuring device storage unit 114 to the terminal device 201, and receives information for operating the blood pressure information measuring device 101 from the terminal device 201. Bluetooth® is used as a communication means in the present embodiment. As another communication means, Near Field radio Communication (NFC), Afero®, Zigbee®, Z-Wave®, wireless LAN, or the like may be used. Or, connection may be performed by wire.

The terminal device 201 is configured to include a terminal device control unit 211, a terminal device storage unit 212, and a terminal device communication unit 213. The terminal device 201 is an information processing device such as a smartphone, a mobile phone, a PHS, or a PDA. Further, the terminal device may not be a general purpose device such as a smartphone but may be a terminal device dedicated to the blood pressure information measuring device.

The terminal device communication unit 213 is a communication interface for communicating with the blood pressure information measuring device 101 and the server device 401. The terminal device communication unit 213 receives the electrocardiogram measurement data and the pulse wave measurement data transmitted from the blood pressure information measuring device 101, and transmits setting information for the blood pressure information measuring device 101, and a request signal of the electrocardiogram measurement data and the pulse wave measurement data. Further, it transmits the electrocardiogram measurement data and the pulse wave measurement data to the server device 401, and receives the request signal of the electrocardiogram measurement data and the pulse wave measurement data from the server device 401. Further, it receives an abnormality notification from the server device 401. In the present embodiment, the communication with the blood pressure information measuring device 101 is Bluetooth® described above, however, other communication means may be used. Further, the communication with the server device 401 can be performed by a wireless LAN via the network 301 such as the Internet.

The terminal device control unit 211 controls storage of the electrocardiogram measurement data and the pulse wave measurement data received by the terminal device communication unit 213 from the blood pressure information measuring device 101 in the terminal device storage unit 212, and controls transmission of the electrocardiogram measurement data and the pulse wave measurement data from the terminal device storage unit 212 to the server device 401.

The terminal device storage unit 212 stores the electrocardiogram measurement data and the pulse wave measurement data received by the terminal device communication unit 213.

A terminal device display unit 214 displays the abnormality notification transmitted from the server device 401.

The server device 401 is configured to include a server device control unit 411, a server device communication unit 412, and a server device storage unit 413.

The server device control unit 411 is configured to include a pulse transit time computation unit 421 as a first computation unit and a blood pressure information computation unit 422 as a second computation unit. The server device control unit 411 (a third computation unit) computes second-order differential data from photoplethysmogram waveform data. The pulse transit time computation unit 421 detects an R wave and a T wave from a waveform profile in the electrocardiogram measurement data described below, detects a P wave and a D wave from a waveform profile in the photoplethysmogram waveform data, and computes the ventricular systolic phase pulse transit time PTT_SYS and the ventricular diastolic phase pulse transit time PTT_DIA based on these information. Further, the blood pressure information computation unit 422 computes the blood pressure information from acceleration pulse wave characteristic information which is based on the second-order differential data described below computed by the server device control unit 411, the ventricular systolic phase pulse transit time PTT_SYS and the ventricular diastolic phase pulse transit time PTT_DIA. Furthermore, the server device control unit 411 determines a health condition of the subject based on the blood pressure information, and notifies the terminal device 201 of an abnormality. The pulse transit time computation unit 421 may use first-order differential data or the second-order differential data of the photoplethysmogram waveform data to detect the R wave and the T wave.

The server device communication unit 412 is a communication interface for communicating with the terminal device 201 via the network 301 such as the Internet. The server device communication unit 412 receives the electrocardiogram measurement data and the pulse wave measurement data transmitted from the terminal device 201, and transmits the request signal of the electrocardiogram measurement data and the pulse wave measurement data to the terminal device 201. Further, it transmits the abnormality notification to the terminal device 201.

The server device storage unit 413 stores the electrocardiogram measurement data and the pulse wave measurement data received by the server device communication unit 412. Further, it stores the blood pressure information computed by the blood pressure information computation unit 422.

<Electrocardiogram Waveform, Photoplethysmogram Waveform, Velocity Pulse Waveform, Acceleration Pulse Waveform, Blood Pressure Information Computation Method>

Figure 4:
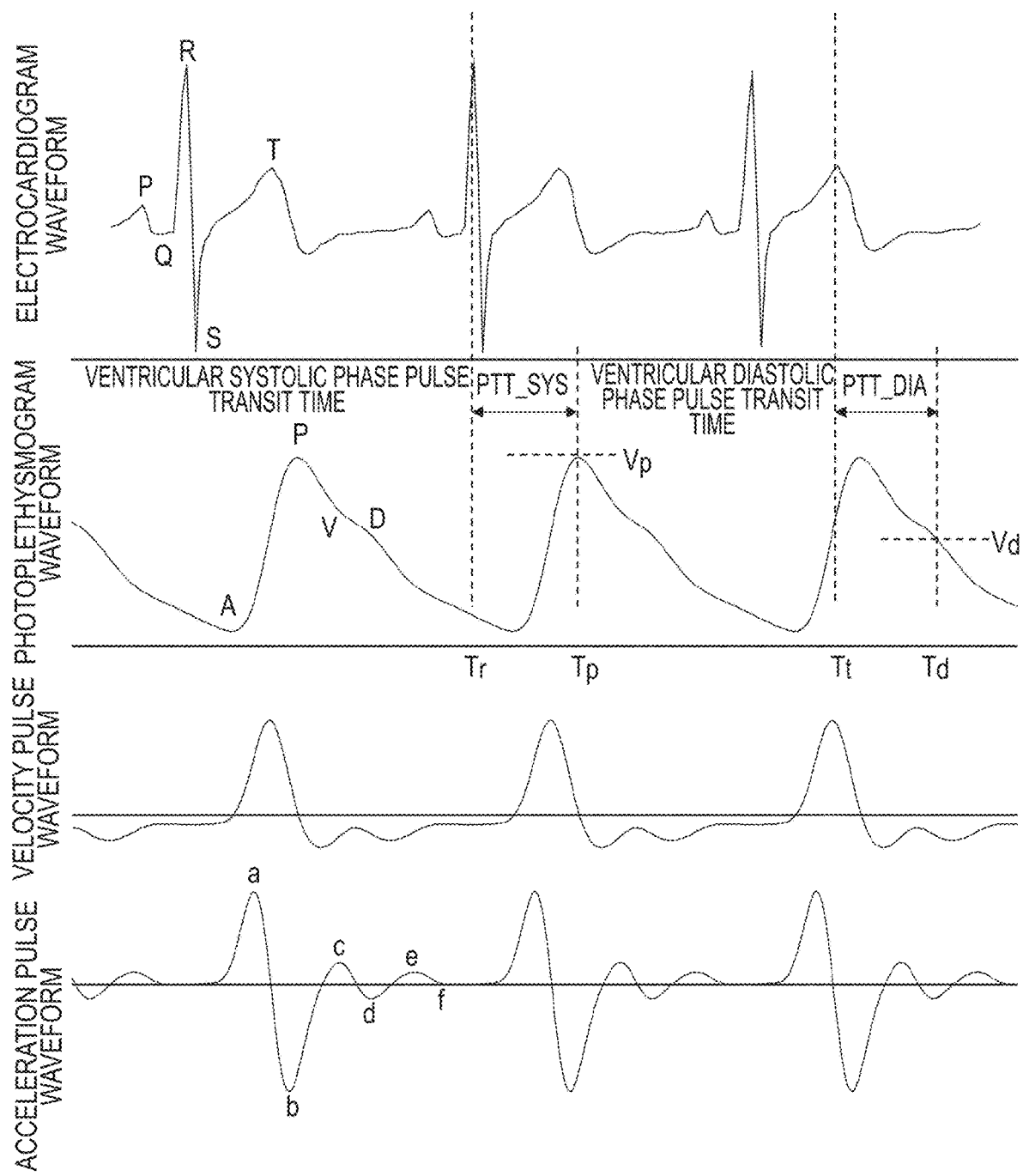
FIG. 4 is a diagram for explaining examples of an electrocardiogram waveform and a pulse wave according to the first embodiment.

FIG. 4 shows the electrocardiogram waveform and the photoplethysmogram waveform of the subject measured by the blood pressure information measuring device 101, and a velocity pulse waveform and an acceleration pulse waveform computed by the server device 401. There are the electrocardiogram waveform, the photoplethysmogram waveform, the velocity pulse waveform, and the acceleration pulse waveform in this order from top of FIG. 4. The vertical axis indicates a strength of each waveform, and the electrocardiogram waveform and the photoplethysmogram waveform are represented by mV indicating the potential. The horizontal axis indicates passage of time, and indicates the passage of time from left to right.

The electrocardiogram waveform is a waveform indicating periodic changes in an electrical signal which causes beating of the human heart. The electrocardiogram waveform indicates one cycle of a heartbeat in which names of P wave, Q wave, R wave, S wave, and T wave are respectively assigned to inflection points of the waveform. The P wave represents atrial contraction, the Q wave, the R wave, and the S wave represent states of ventricular contraction, and the T wave represents onset of ventricular dilatation.

The photoplethysmogram waveform is a waveform indicating changes in blood pressure and volume in a peripheral vascular system associated with the beating of the human heart. The photoplethysmogram waveform indicates one cycle of the heartbeat in which the names of A wave, P wave, V wave, and D wave are respectively assigned to inflection points of the waveform. Using the A wave as a reference point at the time of generation of arterial pulse wave, the P wave represents a Percussion wave (shockwave) generated by left ventricular ejection, the V wave represents a Valley wave (wave due to overlapping ridges) generated at the time of closure of aortic valve, and the D wave represents a Dicrotic wave (overlapping wave) which is a reflected vibrational wave.

The velocity pulse waveform is a first-order differential of the photoplethysmogram waveform in time. The acceleration pulse waveform is a first-order differential of the velocity pulse waveform in time, that is, a second-order differential of the photoplethysmogram waveform. As shown in FIG. 4, in the acceleration pulse waveform, names of a wave (early systolic positive wave), b wave (early systolic negative wave), c wave (mid-systolic reincreasing wave), d wave (late systolic redecreasing wave), e wave (early diastolic positive wave) and f wave (early diastolic negative wave) are respectively assigned to peaks of the waveform. A ratio of b wave intensity to a wave intensity and a ratio of f wave intensity to e wave intensity are parameters indicating stretchability or elasticity of the blood vessel. Main vascular components are Endothelium, Elastin, Collagen, and Smooth Muscle. Each of the components has different properties, and Collagen and Elastin respectively have a strong influence on the elasticity of the blood vessel at the time of the systolic blood pressure and the diastolic blood pressure. Therefore, the elasticity varying depending on a blood pressure value can be expressed by a parameter (b/a) which is the ratio of the b wave intensity to the a wave intensity and a parameter (f/e) which is the ratio of the f wave intensity to the e wave intensity. The values also vary due to effects of age, gender, and environmental variables (such as temperature). Therefore, the values of (b/a) and (f/e) can be calculated as the characteristic information of the acceleration pulse waveform.

As shown in FIG. 4, a time difference between a time Tr at which the R wave is generated and a time Tp at which the P wave is generated is the ventricular systolic phase pulse transit time PTT_SYS. A time difference between a time Tt at which the T wave is generated and a time Td at which the D wave is generated is the ventricular diastolic phase pulse transit time PTT_DIA. That is, as shown by equations (1) and (2), from the time Tr of the R wave and the time Tt of the T wave of the electrocardiogram waveform, and the time Tp of the T wave and the time Td of the D wave of the photoplethysmogram waveform, the ventricular systolic phase pulse transit time PTT_SYS and the ventricular diastolic phase pulse transit time PTT_DIA can be calculated.

$$PTT\_SYS = Tp - Tr \quad (1)$$

$$PTT\_DIA = Td - Tt \quad (2)$$

The first electrode 121 for measuring the electrocardiogram waveform and the optical sensor module 123 for measuring the photoplethysmogram waveform are opposed to each other via the wrist 901, and their arrangement positions are separated from each other, so that a detection site of the electrocardiogram waveform and the measurement site of the photoplethysmogram waveform are separated. Therefore, it is possible to extend an absolute calculation time of the ventricular systolic phase pulse transit time PTT_SYS and the ventricular diastolic phase pulse transit time PTT_DIA by generating a time lag in which characteristic waveforms are generated. Therefore, when obtaining change information of the ventricular systolic phase pulse transit time PTT_SYS and the ventricular diastolic phase pulse transit time PTT_DIA, accuracy of the change information can be improved.

Here, an equation for calculating the blood pressure will be described.

Relationship between pulse wave propagation velocity and a longitudinal elastic modulus of an arterial wall is shown by a pulse wave propagation velocity equation (Moens-Korteweg equation) of equation (3) shown below.

$$L/T\_PTT = \sqrt{(E \cdot h/(2 \cdot r \cdot \rho))} \quad (3)$$

Parameters of the equation (3) are L: inter-measurement distance, T_PTT: pulse transit time, r: blood vessel inner diameter, E: longitudinal elastic modulus of blood vessel, h: blood vessel thickness, $\rho$: blood density.

It is known that the longitudinal elastic modulus and the blood pressure value are in correlation, and it can be shown by the following equation.

$$E = E_0 \cdot \exp(\alpha \cdot P) \quad (4)$$

Here, P: blood pressure value, $\alpha$: constant, $E_0$: initial value.

From the equations (3) and (4), the following equation can be derived.

$$P = (-2 \cdot \ln(T\_PTT) + \ln(2 \cdot r \cdot \rho \cdot L^2/(E_0 \cdot h)))/\alpha \quad (5)$$

In represents natural logarithm. At this time, since "r·$\rho$" is proportional to a blood volume at the measurement site, it can be indicated by a high value (Vp, Vd) shown by the photoplethysmogram waveform. Further, since "$E_0 \cdot h$" is a value proportional to the elasticity of the blood vessel, it can be replaced by using parameters (b/a) and (f/e) indicating the elasticity.

Therefore, the systolic blood pressure BP_SYS (Blood Pressure_Systolic) and the diastolic blood pressure BP_DIA (Blood Pressure_Diastolic) can be expressed by the following equations (6) and (7).

$$BP\_SYS = A1 \cdot \ln(PTT\_SYS) + A2 \cdot \ln(Vp) + A3 \cdot \ln(b/a) + A4 \quad (6)$$

$$BP\_DIA = A5 \cdot \ln(PTT\_DIA) + A6 \cdot \ln(Vd) + A7 \cdot \ln(f/e) + A8 \quad (7)$$

A1 to A8 are constants determined by conditions. The systolic blood pressure BP_SYS which can be calculated by the equation (6) is sum of natural logarithm of the ventricular systolic phase pulse transit time PTT_SYS multiplied by a constant A1, natural logarithm of P wave intensity Vp multiplied by a constant A2, natural logarithm of (b/a) multiplied by a constant A3, and a constant A4. The diastolic blood pressure BP_DIA which can be calculated by the equation (7) is sum of natural logarithm of the ventricular diastolic phase pulse transit time PTT_DIA multiplied by a constant A5, natural logarithm of D wave intensity Vd multiplied by a constant A6, natural logarithm of (f/e) multiplied by a constant A7, and a constant A8. It is possible to obtain the systolic blood pressure BP_SYS and the diastolic blood pressure BP_DIA by determining the constants according to characteristics of the device, a person to be measured, and the like. However, when checking a change state of the systolic blood pressure BP_SYS and the diastolic blood pressure BP_DIA, it is not necessary to determine all the constants, but it is possible to get values as information on the systolic blood pressure BP_SYS and information on the diastolic blood pressure BP_DIA while using provisional values in place of the constants. The natural logarithm of the P wave intensity Vp and the natural logarithm of the D wave intensity Vd are terms in consideration of effects of the blood density. Further, the natural logarithm of (b/a) and the natural logarithm of (f/e) are terms in consideration of effects of the longitudinal elastic modulus of the arterial wall. Therefore, depending on the measurement conditions, the information on the systolic blood pressure BP_SYS and the information on the diastolic blood pressure BP_DIA may be computed by selecting one of the terms and making the other term constant.

<Flow of Processing>

Figure 5:
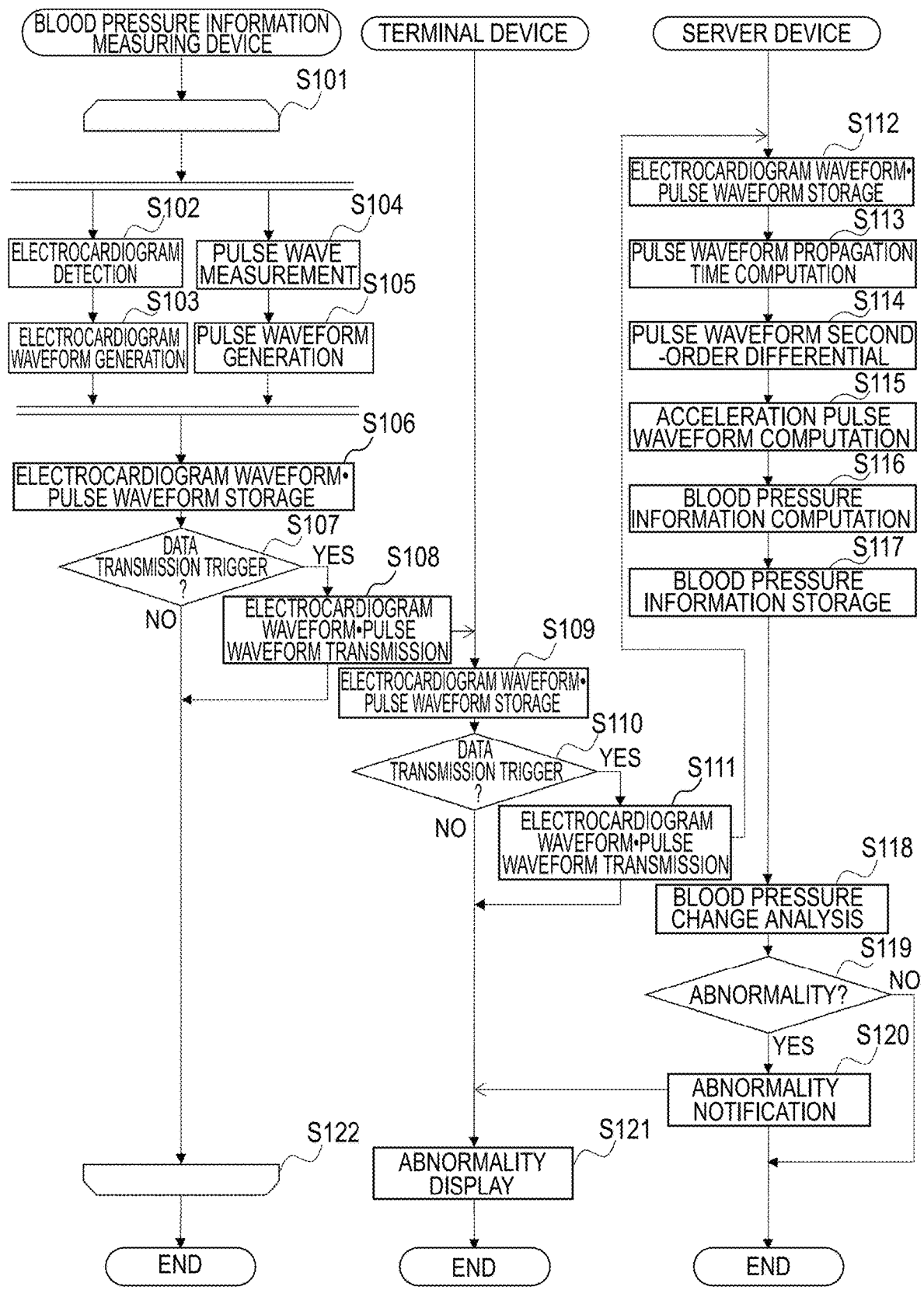
FIG. 5 is a flowchart for explaining an operation of the blood pressure information measuring system according to the first embodiment.

Next, an operation of the blood pressure information measuring system 1 according to the first embodiment of the present invention will be described with reference to a flowchart shown in FIG. 5. The flowchart of FIG. 5 shows related states of operations of the blood pressure information measuring device 101, the terminal device 201, and the server device 401.

In Step S101, the blood pressure information measuring device 101 performs a loop in which the subject starts measurement and performs an end operation, until Step S122.

In Step S102, the electrocardiogram measurement control unit 117 detects the electrocardiogram from the first electrode 121 and the second electrode 122. Note that Steps S102 and S104, and Steps S103 and S105 are simultaneously processed by parallel processing.

In Step S103, the electrocardiogram measurement control unit 117 generates the electrocardiogram waveform from temporal change of the electrocardiogram detected in Step S102.

In Step S104, the pulse wave measurement control unit 118 controls the optical sensor module 123 to detect the pulse wave. Specifically, the pulse wave measurement control unit 118 causes the light emitting LED of the light emitter 124 to emit light to irradiate the wrist 901. The light receiver 125 receives the light reflected from the wrist 901. The light receiver 125 converts the received light into an electrical signal by the photodiode of the light receiver 125, and transmits it to the pulse wave measurement control unit 118 as pulse wave information.

In Step S105, the pulse wave measurement control unit 118 generates the photoplethysmogram waveform from temporal change of the pulse wave information based on the pulse wave detected in Step S104.

In Step S106, the measuring device control unit 113 adds detected times as measurement times to the electrocardiogram waveform generated in Step S103 and the photoplethysmogram waveform generated in Step S105, and stores them as the electrocardiogram measurement data and the pulse wave measurement data (indicated as "electrocardiogram waveform, pulse waveform" in FIG. 5) in the measuring device storage unit 114.

In Step S107, the measuring device control unit 113 determines whether there is a measuring device data transmission trigger. If the measuring device data transmission trigger is "YES", that is, "Y", the flow proceeds to Step S107, and if "NO", that is, "N", the flow proceeds to Step S122. The measuring device data transmission trigger is an internal parameter in the blood pressure information measuring device 101. When the electrocardiogram measurement data and the pulse wave measurement data are constantly transmitted from the blood pressure information measuring device 101 to the terminal device 201, the parameter is always set to "YES", that is, "1". When the electrocardiogram measurement data and the pulse wave measurement data are periodically transmitted from the blood pressure information measuring device 101 to the terminal device 201, the measuring device data transmission trigger is set to "1" at a set timing by an internal counter. Further, in response to a request from the terminal device 201, the measuring device data transmission trigger may be set to "1".

In Step S108, the measuring device control unit 113 transmits the electrocardiogram measurement data and the pulse wave measurement data stored in the measuring device storage unit 114 to the terminal device 201.

In Step S109, the terminal device control unit 211 stores the electrocardiogram measurement data and the pulse wave measurement data received by the terminal device communication unit 213 in the terminal device storage unit 212.

In Step S110, the terminal device control unit 211 determines whether there is a terminal device data transmission trigger. If the terminal device data transmission trigger is "YES", that is, "Y", the flow proceeds to Step S111, and if "NO", that is, "N", the flow proceeds to Step S121. The terminal device data transmission trigger is an internal parameter in the terminal device 201. When the electrocardiogram measurement data and the pulse wave measurement data are constantly transmitted from the terminal device 201 to the server device 401, the parameter is always set to "YES", that is, "1". When the electrocardiogram measurement data and the pulse wave measurement data are periodically transmitted to the server device 401 from the terminal device 201, the terminal device data transmission trigger is set to "1" at a set timing by an internal counter. Further, in response to a request from the server device 401, the terminal device data transmission trigger may be set to "1".

In Step S111, the terminal device control unit 211 transmits the electrocardiogram measurement data and the pulse wave measurement data stored in the terminal device storage unit 212 to the server device 401.

In Step S112, the server device control unit 411 stores the electrocardiogram measurement data and the pulse wave measurement data received by the server device communication unit 412 in the server device storage unit 413.

In Step S113, the server device control unit 411 computes the pulse transit time from the electrocardiogram measurement data and the pulse wave measurement data stored in the server device storage unit 413. A specific operation procedure will be described below. The pulse transit time computation unit 421 extracts the waveform profile in the electrocardiogram measurement data and the waveform profile in the pulse wave measurement data, which are close in measurement timing. Next, the pulse transit time computation unit 421 detects the R wave and T wave from the waveform profile in the electrocardiogram measurement data, and stores the detected time information of generation of the R wave and T wave as Tr and Tt. Similarly, the pulse transit time computation unit 421 detects the P wave and the D wave from the waveform profile in the photoplethysmogram waveform data, and stores the detected time information of generation of the P wave and the D wave as Tp and Td. At the same time, the P wave intensity Vp and the D wave intensity Vd are detected and stored. As shown in FIG. 4, the pulse transit time computation unit 421 computes the difference between the time information Tr at which the R wave is generated and the time information Tp at which the P wave is generated to compute the ventricular systolic phase pulse transit time PTT_SYS. Similarly, the difference between the time information Tt at which the T wave is generated and the time information Td at which the D wave is generated is computed to compute the ventricular diastolic phase pulse transit time PTT_DIA.

In Step S114, the server device control unit 411 computes the second-order differential data from the photoplethysmogram waveform data stored in the server device storage unit 413. Specifically, as shown in FIG. 4, the first-order differential of the photoplethysmogram waveform data is performed, and the data subjected to the first-order differential is further differentiated to obtain the second-order differential data. The waveform obtained by second-order differentiation of the pulse wave is called the acceleration pulse waveform.

In Step S115, the server device control unit 411 computes the characteristic information of the acceleration pulse waveform from the second-order differential data obtained in Step S114. The characteristic information of the acceleration pulse waveform is obtained by performing computation from the intensities of the a wave, b wave, e wave, and f wave indicating the peaks of the acceleration pulse waveform described above.

In Step S116, the server device control unit 411 computes the blood pressure information from the ventricular systolic phase pulse transit time PTT_SYS, the ventricular diastolic phase pulse transit time PTT_DIA, which are obtained in Step S113, and the characteristic information of the acceleration pulse waveform obtained in Step S115. The server device control unit 411 computes the blood pressure information on the systolic blood pressure from the ventricular systolic phase pulse transit time PTT_SYS and the characteristic information of the acceleration pulse wave, and computes the blood pressure information on the diastolic blood pressure from the ventricular diastolic phase pulse transit time PTT_DIA and the characteristic information of the acceleration pulse wave. The computation is performed using the equations (6) and (7) described above.

In Step S117, the server device control unit 411 stores the blood pressure information computed in Step S116 in the server device storage unit 413.

In Step S118, the server device control unit 411 analyzes the change state of the blood pressure information stored in the server device storage unit 413. If it is determined that the change state is deterioration of the health condition of the subject, a determination flag is set to "YES" as abnormal. The determination flag is an internal parameter of the server device 401.

In Step S119, the server device control unit 411 determines whether the determination flag is "YES". If "YES", the flow proceeds to Step S120, and if "NO", the flow is ended.

In Step S120, the server device control unit 411 notifies the terminal device 201 of the abnormality via the server device communication unit 412.

In Step S121, the terminal device control unit 211 controls display for notifying the terminal device display unit 214 that there is the abnormality in the health condition based on the abnormality notification received by the terminal device communication unit 213. Thus, the terminal device 201 can notify the subject of the abnormality in the health condition.

In Step S122, the blood pressure information measuring device 101 performs a loop with Step S101 until the power of the blood pressure information measuring device 101 is turned off or the measuring device control unit 113 performs an operation of ending measurement.

<Description of Effects>

As described above, the blood pressure information measuring system 1 according to the first embodiment of the present invention uses the R wave and T wave of the electrocardiogram waveform, and the P wave and D wave of the photoplethysmogram waveform, so that changes in the ventricular systolic phase pulse transit time PTT_SYS and the ventricular diastolic phase pulse transit time PTT_DIA can be measured. Therefore, the blood pressure information measuring system 1 computes the blood pressure information on the systolic blood pressure from the ventricular systolic phase pulse transit time PTT_SYS and the characteristic information of the acceleration pulse wave, and computes the blood pressure information on the diastolic blood pressure, from the ventricular diastolic phase pulse transit time PTT_DIA and the characteristic information of the acceleration pulse wave, so that an accurate change related to the blood pressure information can be detected.

In addition, the blood pressure information measuring system 1 can detect the change in blood pressure information accurately, thereby discovering the deterioration of the health condition early, and appropriately managing the health condition of the subject.

In the present embodiment, by correlating the blood pressure measured using another blood pressure measuring unit, the blood pressure information on the systolic blood pressure and the blood pressure information on the diastolic blood pressure measured by the blood pressure information measuring system 1, it is also possible to output blood pressure information as an absolute value of blood pressure.

In the present embodiment, the blood pressure information measuring device 101 and the terminal device 201 may be integrally configured, and the blood pressure information measuring device 101 and the server device 401 may communicate with each other.

The terminal device display unit 214 may display the blood pressure information and the pulse wave information computed by the server device 401.

The blood pressure information measuring device 101 may be configured such that a third electrode is added adjacent to the first electrode 121, and the first electrode and the third electrode are arranged equidistant from the radial artery 911 for detection. In this case, random noise can be removed by using an additional amplifier circuit with respect to detection values from the first electrode 121 and the third electrode, thereby improving measurement accuracy of the electrocardiogram waveform. Another electrode may be further added to improve the effect in addition to the third electrode.

Second Embodiment

<Configuration>

Figure 6:
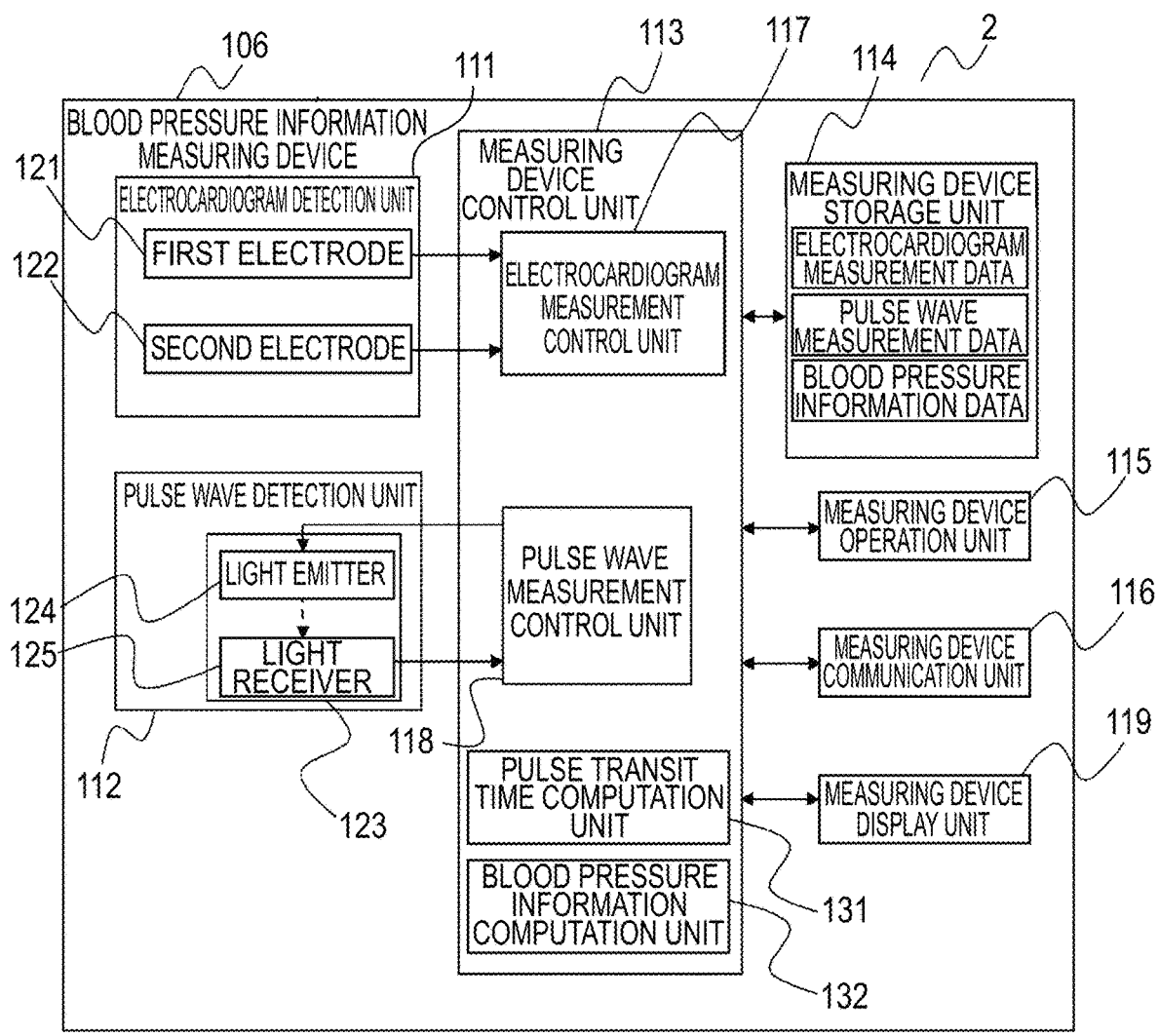
FIG. 6 is a schematic block diagram showing a configuration of the blood pressure information measuring system according to a second embodiment.

The configuration and outline of a blood pressure information measuring system 2 in a second embodiment will be described with reference to FIG. 6. FIG. 6 is a block diagram of a blood pressure information measuring device 106 constituting the blood pressure information measuring system 2 of the present embodiment. Since a mounted state on the arm of the subject, a relationship between the blood pressure information measuring device 106 and the arm, the electrocardiographic waveform, the photoplethysmogram waveform and the like are the same as in the first embodiment, descriptions thereof will be omitted.

The blood pressure information measuring device 106 is configured to include the electrocardiogram detection unit 111, the pulse wave detection unit 112, the measuring device control unit 113, the measuring device storage unit 114, the measuring device operation unit 115, the measuring device communication unit 116, and a measuring device display unit 119.

The electrocardiogram detection unit 111 is configured to include the first electrode 121 for detecting the electrocardiogram of the radial artery and the second electrode 122 for measuring the living body reference potential.

The pulse wave detection unit 112 is configured to include the optical sensor module 123. The optical sensor module 123 includes the light emitter 124 and the light receiver 125.

The measurement device control unit 113 is configured to include the electrocardiogram measurement control unit 117, the pulse wave measurement control unit 118, a pulse transit time computation unit 131 which is a first computation unit, and a blood pressure information computation unit 132 which is a second computation unit. The electrocardiogram measurement control unit 117 detects the difference between the detection potentials from the first electrode 121 and the second electrode 122, and adds time information to form the electrocardiogram waveform. The pulse wave measurement control unit 118 performs light emission control of the light emitter 124 of the pulse wave detection unit 112, and receives the detection signal from the light receiver 125. The measuring device control unit 113 computes the second-order differential data from the photoplethysmogram waveform data. The pulse transit time computation unit 131 detects the R wave and the T wave from the waveform profile in the electrocardiogram measurement data, detects the P wave and the D wave from the waveform profile in the photoplethysmogram waveform data, and computes the ventricular systolic phase pulse transit time PTT_SYS and the ventricular diastolic phase pulse transit time PTT_DIA based on these information. Further, the blood pressure information computation unit 132 computes the blood pressure information from the acceleration pulse wave characteristic information which is based on the second-order differential data of the pulse waveform data computed by the measuring device control unit 113, the ventricular systolic phase pulse transit time PTT_SYS and the ventricular diastolic phase pulse transit time PTT_DIA. Furthermore, the measuring device control unit 113 determines the health condition of the subject based on the blood pressure information, and notifies the measuring device display unit 119 of the abnormality. The pulse transit time computation unit 131 may use the first-order differential data or the second-order differential data of the photoplethysmogram waveform data to detect the R wave and the T wave.

The measuring device storage unit 114 stores the electrocardiogram measurement data received by the electrocardiogram measurement control unit 117, and stores the pulse wave measurement data received by the pulse wave measurement control unit 118. In addition, the blood pressure information computed by the measuring device control unit 113 is stored. The electrocardiogram measurement data is the information on the electrocardiogram waveform in which the electrocardiogram information detected by the first electrode 121 is continuously arranged, and is added with the measurement time information and the like of the electrocardiogram waveform. The pulse wave measurement data is the information on the photoplethysmogram in which the pulse wave detected by the optical sensor module 123 is continuously arranged, and is added with the measurement time information and the like of the photoplethysmogram waveform.

The measuring device operation unit 115 is an operation unit for the subject or the like to perform the operation of the power supply of the blood pressure information measuring device 106 and the operation such as measurement start and end.

The measuring device communication unit 116 is a communication interface for communicating the blood pressure information measuring device 106 with the external devices. The measuring device communication unit 116 can transmit the electrocardiographic measurement data, the pulse wave measurement data, and the blood pressure information.

<Flow of Processing>

Figure 7:
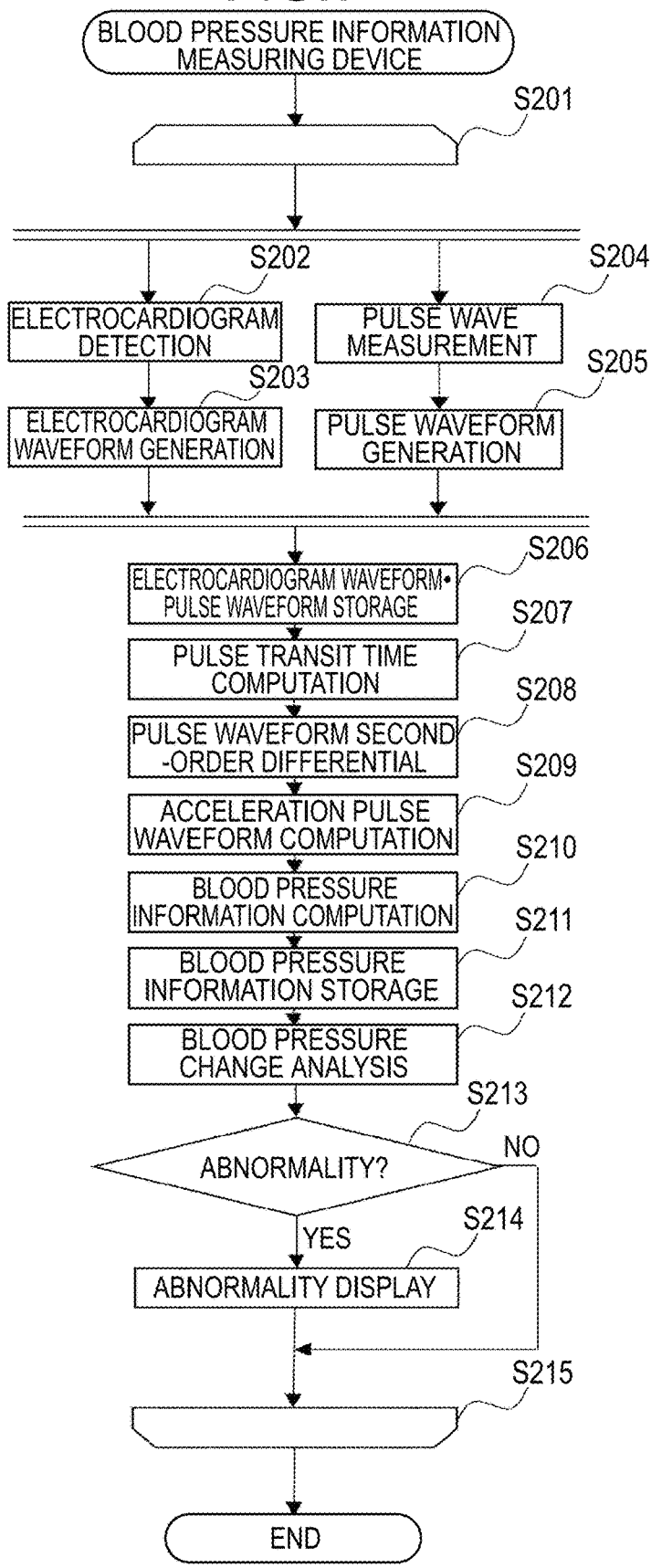
FIG. 7 is a flowchart for explaining an operation of the blood pressure information measuring system according to the second embodiment.

Next, the operation of the blood pressure information measurement system 2 according to the second embodiment of the present invention will be described with reference to a flowchart shown in FIG. 7. The flowchart of FIG. 7 shows the blood pressure information measuring device 106.

In Step S201, the blood pressure information measuring device 106 performs a loop in which the subject starts measurement and performs an end operation, from S201 to S2015.

In Step S202, the electrocardiogram measurement control unit 117 detects the electrocardiogram from the first electrode 121 and the second electrode 122. Steps S202 and S204, and Steps S203 and S205 are simultaneously processed by parallel processing.

In Step S203, the electrocardiogram measurement control unit 117 generates the electrocardiogram waveform from the temporal change of the electrocardiogram detected in Step S202.

In Step S204, the pulse wave measurement control unit 118 controls the optical sensor module 123 to detect the pulse wave. Specifically, the pulse wave measurement control unit 118 causes the light emitting LED of the light emitter 124 to emit light to irradiate the wrist 901. The light receiver 125 receives the light reflected from the wrist 901. The light receiver 125 converts the received light into the electrical signal by the photodiode of the light receiver 125, and transmits it to the pulse wave measurement control unit 118 as the pulse wave information.

In Step S205, the pulse wave measurement control unit 118 generates the photoplethysmogram waveform from temporal change of the pulse wave information based on the pulse wave detected in Step S204.

In Step S206, the measuring device control unit 113 adds detected times as measurement times to the electrocardiogram waveform generated in Step S203 and the photoplethysmogram waveform generated in Step S205, and stores them as the electrocardiogram measurement data and the pulse wave measurement data (indicated as "electrocardiogram waveform, pulse waveform" in FIG. 7) in the measuring device storage unit 114.

In Step S207, the measuring device control unit 113 computes the pulse transit time from the electrocardiogram measurement data and the pulse wave measurement data stored in the measuring device storage unit 114. The specific operation procedure will be described below. The pulse transit time computation unit 131 extracts the waveform profile in the electrocardiogram measurement data and the waveform profile in the pulse wave measurement data, which are close in measurement timing. Next, the pulse transit time computation unit 131 detects the R wave and T wave from the waveform profile in the electrocardiogram measurement data, and stores the detected time information of generation of the R wave and T wave as Tr and Tt. Similarly, the pulse transit time computation unit 131 detects the P wave and the D wave from the waveform profile in the photoplethysmogram waveform data, and stores the detected time information of generation of the P wave and the D wave as Tp and Td. At the same time, the P wave intensity Vp and the D wave intensity Vd are detected and stored. The pulse transit time computation unit 131 computes the difference between the time information Tr at which the R wave is generated and the time information Tp at which the P wave is generated to compute the ventricular systolic phase pulse transit time PTT_SYS. Similarly, the difference between the time information Tt at which the T wave is generated and the time information Td at which the D wave is generated is computed to compute the ventricular diastolic phase pulse transit time PTT_DIA.

In Step S208, the measuring device control unit 113 computes the second-order differential data from the photoplethysmogram waveform data stored in the measuring device storage unit 114. Specifically, the first-order differential of the photoplethysmogram waveform data is performed, and the data subjected to the first-order differential is further differentiated to obtain the second-order differential data. The waveform obtained by second-order differentiation of the pulse wave is called the acceleration pulse waveform.

In Step S209, the measuring device control unit 113 computes the characteristic information of the acceleration pulse waveform from the second-order differential data obtained in Step S208. The characteristic information of the acceleration pulse waveform is obtained by performing the computation from the intensities of the a wave, b wave, e wave, and f wave indicating the peaks of the acceleration pulse waveform.

In Step S210, the measuring device control unit 113 computes the blood pressure information from the ventricular systolic phase pulse transit time PTT_SYS, the ventricular diastolic phase pulse transit time PTT_DIA, which are obtained in Step S207, and the characteristic information of the acceleration pulse waveform obtained in Step S209. The measuring device control unit 113 computes the blood pressure information on the systolic blood pressure from the ventricular systolic phase pulse transit time PTT_SYS and the characteristic information of the acceleration pulse waveform, and computes the blood pressure information on the diastolic blood pressure from the ventricular diastolic phase pulse transit time PTT_DIA and the characteristic information of the acceleration pulse wave. The computation is performed using the equations (6) and (7) shown in the first embodiment.

In Step S211, the measuring device control unit 113 stores the blood pressure information computed in Step S210 in the measuring device storage unit 114.

In Step S212, the measuring device control unit 113 analyzes the change state of the blood pressure information stored in the measuring device storage unit 114. If it is determined that the change state is deterioration of the health condition of the subject, the determination flag is set to "YES" as abnormal. The determination flag is the internal parameter of the blood pressure information measuring device 106.

In Step S213, the measuring device control unit 113 determines whether the determination flag is "YES". If "YES", the flow proceeds to Step S214, and if "NO", the flow proceeds to Step S215.

In Step S214, the measuring device control unit 113 controls display for notifying the measuring device display unit 119 that there is the abnormality in the health condition. Thus, the blood pressure information measuring device 106 can notify the subject of the abnormality in the health condition.

In Step S215, the blood pressure information measuring device 106 performs a loop from S201 to S2015 until the power of the blood pressure information measuring device 106 is turned off or the measuring device operation unit 115 performs the operation of ending measurement.

<Description of Effects>

As described above, the blood pressure information measuring system 2 according to the second embodiment of the present invention uses the R wave and T wave of the electrocardiogram waveform, and the P wave and D wave of the photoplethysmogram waveform, so that changes in the ventricular systolic phase pulse transit time PTT_SYS and the ventricular diastolic phase pulse transit time PTT_DIA can be measured only with the blood pressure information measuring device 106 alone mounted on the arm. Therefore, the blood pressure information measuring system 2 computes the blood pressure information on the systolic blood pressure from the ventricular systolic phase pulse transit time PTT_SYS and the characteristic information of the acceleration pulse waveform, and computes the blood pressure information on the diastolic blood pressure, from the ventricular diastolic phase pulse transit time PTT_DIA and the characteristic information of the acceleration pulse waveform, so that the accurate change related to the blood pressure information can be detected.

In addition, the blood pressure information measuring system 2 can detect the change in blood pressure information accurately, thereby discovering the deterioration of the health condition early, and appropriately managing the health condition of the subject.

In the present embodiment, by correlating the blood pressure measured using another blood pressure measuring unit, the blood pressure information on the systolic blood pressure and the blood pressure information on the diastolic blood pressure measured by the blood pressure information measuring system 2, it is also possible to output blood pressure information as an absolute value of blood pressure.

The measuring device display unit 119 may display the blood pressure information and the pulse wave information.

Third Embodiment

<Configuration>

Figure 9:
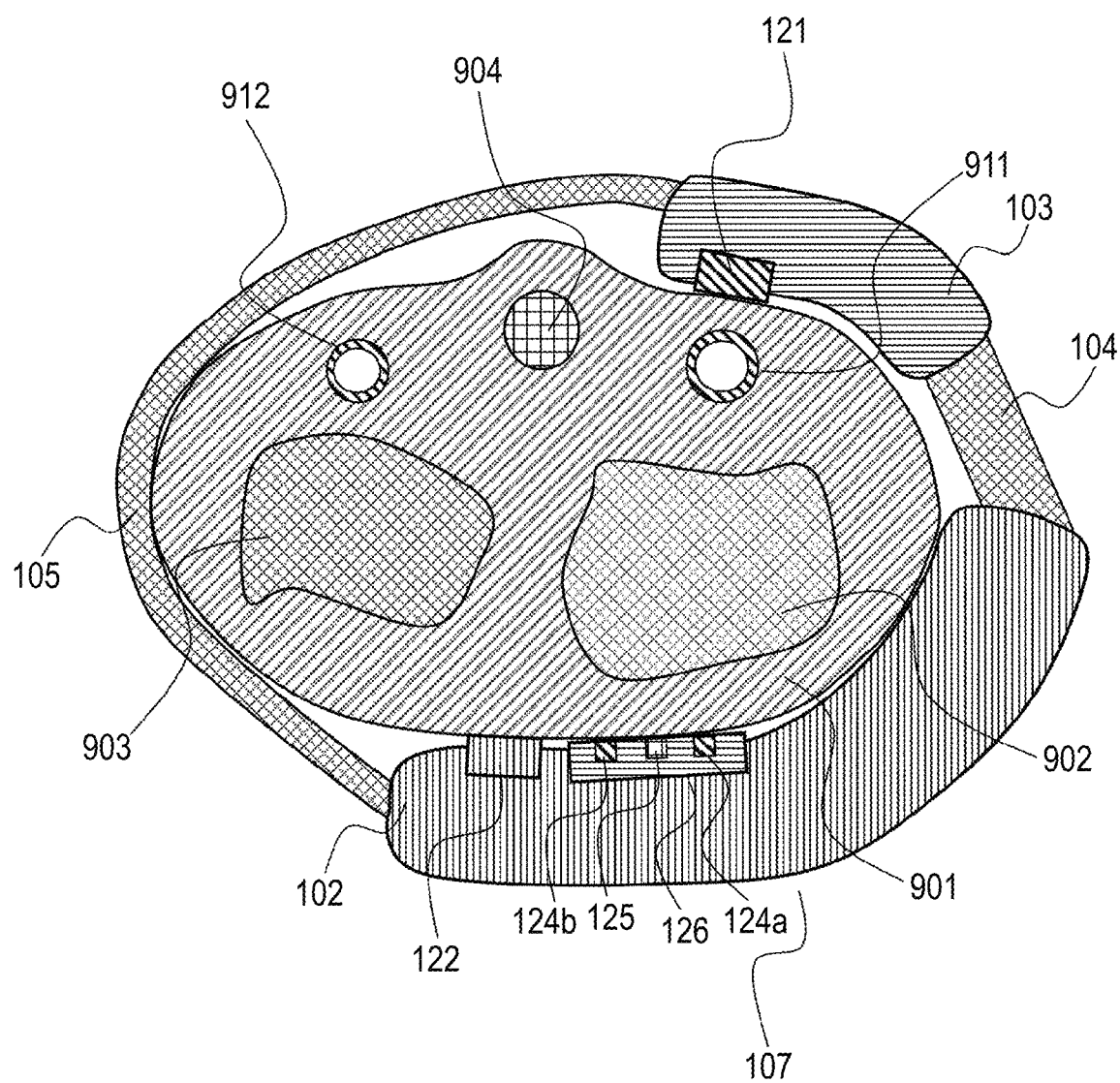
FIG. 9 is a view for explaining the left arm of the subject wearing the blood pressure information measuring device according to the third embodiment, and a cross-section taken along a line B-B in FIG. 8A of the blood pressure information measuring device.

The arm which is the measurement site of the subject by a blood pressure information measuring system 3 according to a third embodiment of the present invention and a blood pressure information measuring device 107 will be described. FIG. 8A is a state in which the blood pressure information measuring device is mounted on the left arm of the subject. FIG. 8B is a view showing the radial artery and the ulnar artery in the left arm of the subject in a transparent manner, and showing the positional relationship between the radial artery and the electrode of the blood pressure information measuring device. FIG. 8C is a view showing the positional relationship between the arm of the subject, the electrode of the blood pressure information measuring device 107, and an optical sensor module 126. FIG. 9 shows a cross-section taken along a line B-B in FIG. 8A. A clear difference from the blood pressure information measuring system 1 according to the first embodiment is that the light emitter 124 is two of 124a and 124b and is disposed to sandwich the light receiver 125.

As shown in FIG. 8A and FIG. 9, the blood pressure information measuring device 107 includes the main unit 102 and the subunit 103, and one ends of the main unit 102 and the subunit 103 are connected to each other by the link band 104 made of rubber with electrical wiring disposed therein. Further, the other ends of the main unit 102 and the subunit 103 are connected to each other by the rubber support band 105 for fixing the blood pressure information measuring device 107 to the wrist 901. With such a configuration, the link band 104 can be deformed, and the main unit 102 and the subunit 103 can be pulled together by the rubber elasticity of the support band 105. Therefore, the subject can bring the main unit 102 and the subunit 103 into close contact with the wrist 901 of the subject regardless of thickness of the wrist 901. Note that the main unit 102 and the subunit 103 may be configured to communicate wirelessly without being connected by the electrical wiring. Further, the support band 105 may be matched to the diameter of the wrist by means of the buckle and the hole as two bands like the watch belt.

The main unit 102 is configured to include the second electrode 122, the optical sensor module 126, the measuring device control unit 113 and the like. The main unit 102 includes the measuring device control unit 113 and the like described below. The subunit 103 is provided with the first electrode 121.

As shown in FIG. 8B and FIG. 9, the radial artery 911 and the ulnar artery 912 pass through the arm of the subject. As shown in FIG. 9, the wrist 901 has the radius 902 and the ulna 903 passing therethrough, the radial artery 911 passes between the radius 902 and the skin on the surface of the wrist, and the ulnar artery 912 passes between the ulna 903 and the skin on the surface of the wrist. The radial artery 911 and the ulnar artery 912 are branched from the brachial artery 913 in the upper arm. The tendon 904 is between the radial artery 911 and the ulnar artery 912. The tendon 904 may protrude to raise the skin on the surface of the wrist by movement of the wrist 901. Therefore, as shown in FIG. 9, the main unit 102 and the subunit 103 of a blood pressure information measuring device 107 do not easily touch the skin near the tendon 904, which can make it difficult for the subject to feel discomfort in wearing.

The first electrode 121 shown in FIG. 8B and FIG. 9 is disposed near the ulnar artery on the back side of hand of the wrist 901, and detects the potential associated with the electrocardiogram from the ulnar artery. The ulnar artery 912 is branched with the radial artery 911 from the brachial artery 913, and distances from the branch portion is substantially equal near the wrist, so that the electrocardiographic waveform can be obtained also in the ulnar artery. The second electrode 122 shown in FIG. 8C and FIG. 9 is disposed on the palm side of the wrist 901, and detects the living body reference potential. With such a configuration, by measuring the potential detected by the first electrode 121 with the second electrode 122 as the reference potential as time passes, it is possible to obtain the electrocardiogram and measure the electrocardiogram waveform. In addition, since the second electrode 122 can suppress variation of the measured reference potential, it is possible to improve the detection accuracy of the electrocardiogram waveform accompanied by the minute change of the T wave and the like, and to accurately measure the change in the ventricular diastolic phase pulse transit time PTT_DIA.

As shown in FIG. 8C and FIG. 9, the optical sensor module 126 is configured to include light emitters 124a, 124b and the light receiver 125. The light emitters 124a, 124b are light emitting LEDs having the center wavelength of 660 nm, and the light receiver 125 is formed of the photodiode capable of receiving light emitted from the light emitters 124a, 124b formed of the light emitting LED. The light emitted from the light emitters 124a, 124b to the wrist is reflected inside the wrist and received by the light receiver 125. The temporal change in intensity of the light received by the light receiver 125 makes it possible to detect the pulse wave caused by the heartbeat of the subject and to measure the photoplethysmogram waveform. Since the light emitters 124a, 124b are arranged to sandwich the light receiver 125, even when the optical sensor module 126 and the arm do not contact in parallel, the light from the light emitters 124a or the light emitter 124b can easily reach the light receiver 125, so that the detection accuracy can be improved. The optical sensor module 126 is disposed on the palm side of the wrist 901, and is disposed at the position facing the first electrode 121 via the wrist 901. This makes it possible to separate the measurement site of the electrocardiogram waveform to be measured by the first electrode 121 and the measurement site of the photoplethysmogram waveform to be measured by the optical sensor module 126. Thus, it is possible to lengthen the ventricular systolic phase pulse transit time PTT_SYS and the ventricular diastolic phase pulse transit time PTT_DIA, thereby improving the reliability of measurement.

<Description of Effects>

As described above, in the blood pressure information measuring system 3 according to the third embodiment of the present invention, since the light emitters 124a and 124b are arranged to sandwich the light receiver 125 in the optical sensor module 126, the detection accuracy of the pulse wave can be improved, and the measurement accuracy of the D-wave, which is weaker in intensity than the P-wave, can be improved. Therefore, the blood pressure information measuring system 3 can accurately calculate the ventricular diastolic phase pulse transit time PTT_DIA using the D wave, thereby improving the accuracy of the information on the diastolic blood pressure.

Fourth Embodiment

<Configuration>

Figure 11:
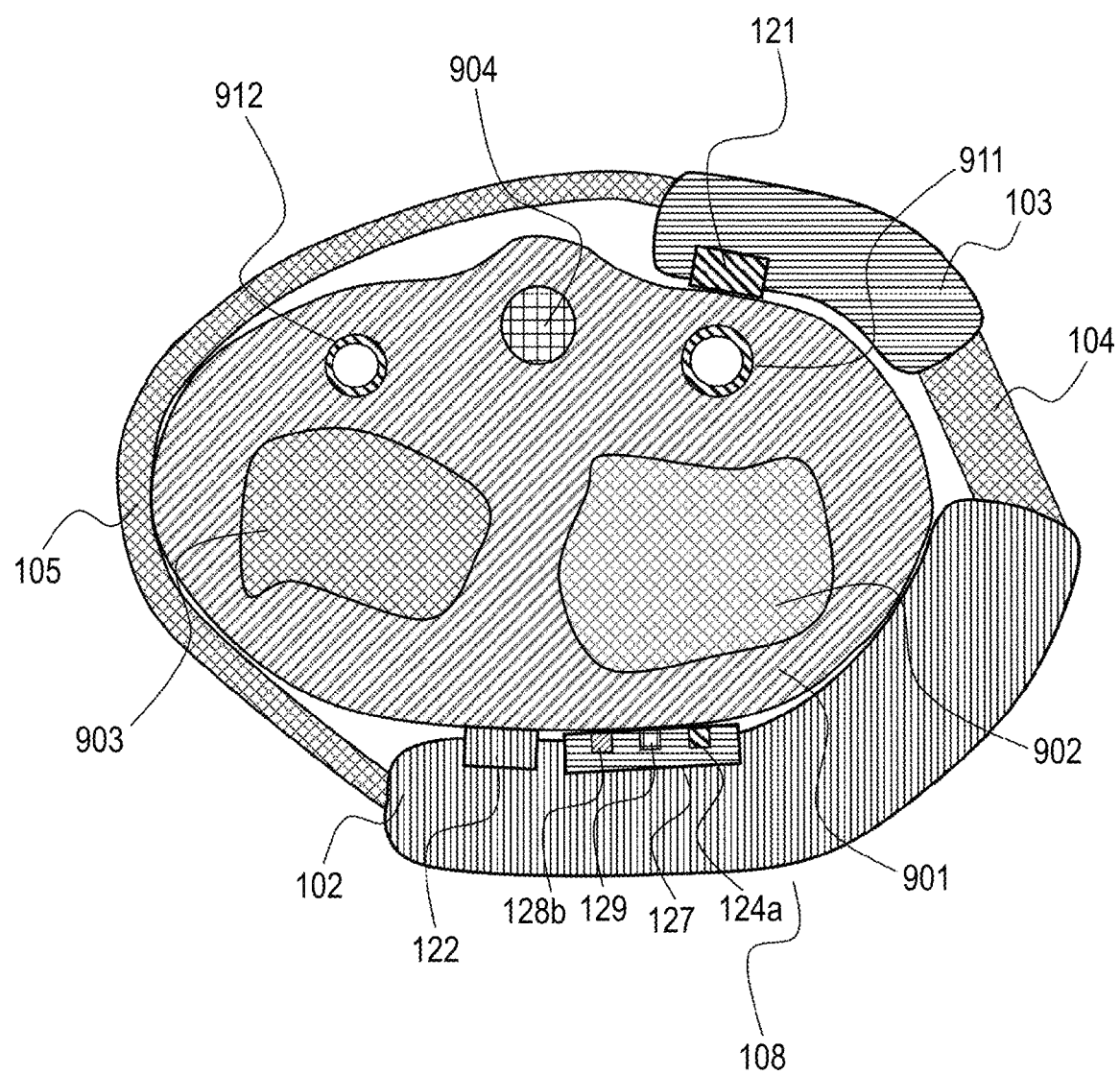
FIG. 11 is a view for explaining the left arm of the subject wearing the blood pressure information measuring device according to the fourth embodiment, and a cross-section taken along a line C-C in FIG. 10A of the blood pressure information measuring device.

The arm which is the measurement site of the subject by a blood pressure information measuring system 4 according to a fourth embodiment of the present invention and a blood pressure information measuring device 108 will be described. FIG. 10A is a state in which the blood pressure information measuring device is mounted on the left arm of the subject. FIG. 10B is a view showing the radial artery and the ulnar artery in the left arm of the subject in the transparent manner, and showing the positional relationship between the radial artery and the electrode of the blood pressure information measuring device. FIG. 10C is a view showing the positional relationship between the arm of the subject, the electrode of the blood pressure information measuring device 108, and an optical sensor module 127. FIG. 11 shows a cross-section taken along a line C-C in FIG. 10A. The clear difference from the blood pressure information measuring system 3 according to the third embodiment is that the light emitter 124 is additionally made of two green light emitting LEDs of 124a, 124b and two blue light emitting LEDs of 128a, 128b, and is disposed to sandwich the light receiver 129.

As shown in FIG. 10A and FIG. 11, the blood pressure information measuring device 108 includes the main unit 102 and the subunit 103, and one ends of the main unit 102 and the subunit 103 are connected to each other by the link band 104 made of rubber with electrical wiring disposed therein. Further, the other ends of the main unit 102 and the subunit 103 are connected to each other by the rubber support band 105 for fixing the blood pressure information measuring device 108 to the wrist 901. With such a configuration, the link band 104 can be deformed, and the main unit 102 and the subunit 103 can be pulled together by the rubber elasticity of the support band 105. Therefore, the subject can bring the main unit 102 and the subunit 103 into close contact with the wrist 901 of the subject regardless of thickness of the wrist 901. Note that the main unit 102 and the subunit 103 may be configured to communicate wirelessly without being connected by the electrical wiring. Further, the support band 105 may be matched to the diameter of the wrist by means of the buckle and the hole as two bands like the watch belt.

The main unit 102 is configured to include the second electrode 122, the optical sensor module 127, the measuring device control unit 113 and the like. The main unit 102 includes the measuring device control unit 113 and the like described below. The subunit 103 is provided with the first electrode 121.

As shown in FIG. 10B and FIG. 11, the radial artery 911 and the ulnar artery 912 pass through the arm of the subject. As shown in FIG. 11, the wrist 901 has the radius 902 and the ulna 903 passing therethrough, the radial artery 911 passes between the radius 902 and the skin on the surface of the wrist, and the ulnar artery 912 passes between the ulna 903 and the skin on the surface of the wrist. The radial artery 911 and the ulnar artery 912 are branched from the brachial artery 913 in the upper arm. The tendon 904 is between the radial artery 911 and the ulnar artery 912. The tendon 904 may protrude to raise the skin on the surface of the wrist by movement of the wrist 901. Therefore, as shown in FIG. 11, the main unit 102 and the subunit 103 of a blood pressure information measuring device 108 do not easily touch the skin near the tendon 904, which can make it difficult for the subject to feel discomfort in wearing.

The first electrode 121 shown in FIG. 10B and FIG. 11 is disposed near the ulnar artery on the back side of hand of the wrist 901, and detects the potential associated with the electrocardiogram from the ulnar artery. The ulnar artery 912 is branched with the radial artery 911 from the brachial artery 913, and distances from the branch portion is substantially equal near the wrist, so that the electrocardiographic waveform can be obtained also in the ulnar artery.

The second electrode 122 shown in FIG. 10C and FIG. 11 is disposed on the palm side of the wrist 901, and detects the living body reference potential. With such a configuration, by measuring the potential detected by the first electrode 121 with the second electrode 122 as the reference potential as time passes, it is possible to obtain the electrocardiogram and measure the electrocardiogram waveform. In addition, since the second electrode 122 can suppress variation of the measured reference potential, it is possible to improve the detection accuracy of the electrocardiogram waveform accompanied by the minute change of the T wave and the like, and to accurately measure the change in the ventricular diastolic phase pulse transit time PTT_DIA.

As shown in FIGS. 10C and 11, the optical sensor module 127 is configured to include the light emitters 124a, 124b, a light receiver 129, and the light emitters 128a, 128b. The light emitters 124a, 124b are green light emitting LEDs having a center wavelength of 520 nm, and the light emitters 128a, 128b are blue light emitting LEDs having a center wavelength of 470 nm. The light receiver 129 is formed of the photodiode capable of receiving light emitted from the light emitters 124a, 124b including the green light emitting LED and the light emitters 128a, 128b including the blue light emitting LED. The green light emitted from the light emitters 124a, 124b to the wrist or the blue light emitted from the light emitters 128a, 128b to the wrist is reflected inside the wrist and received by the light receiver 129. The temporal change in intensity of the light received by the light receiver 129 makes it possible to detect the pulse wave caused by the heartbeat of the subject, and to measure the photoplethysmogram waveform. By changing a light emission wavelength, it is possible to change a focal length from each light emitter to the measurement site. Since the blood vessel for measurement is close to a surface of the skin, the measurement accuracy can be improved by using a short wavelength of 470 nm or 520 nm as the center wavelength. When the subject is resting, a stable measurement can be performed using the green light emitting LED. When the subject is active, the stable measurement can be performed using the blue light emitting LED, which is remarkable particularly when color of the skin is Skin Type V according to Fitzpatrick scale. Therefore, an acceleration sensor or the like is provided in the blood pressure information measuring device 108, an activity state of the subject is recognized, and the light emitters 124a, 124b and the light emitters 128a, 128b are switched depending on the activity state, so that the detection accuracy of the pulse wave can be improved.

<Description of Effects>

As described above, the blood pressure information measuring system 4 according to the fourth embodiment of the present invention can improve the accuracy of the blood pressure information, by switching between the green light emitting LED and the blue light emitting LED depending on the activity state of the subject, improving the measurement accuracy of the pulse wave, and accurately determining the times of the P wave and the D wave.

In the present embodiment, the green light emitting LED and the blue light emitting LED are switched depending on the activity state of the subject, however, the green light emitting LED and the blue light emitting LED may be simultaneously emitted. In this case, configuration for measuring the activity state and configuration for switching between the green light emitting LED and the blue light emitting LED are unnecessary.

Fifth Embodiment

<Configuration>

Figure 13:
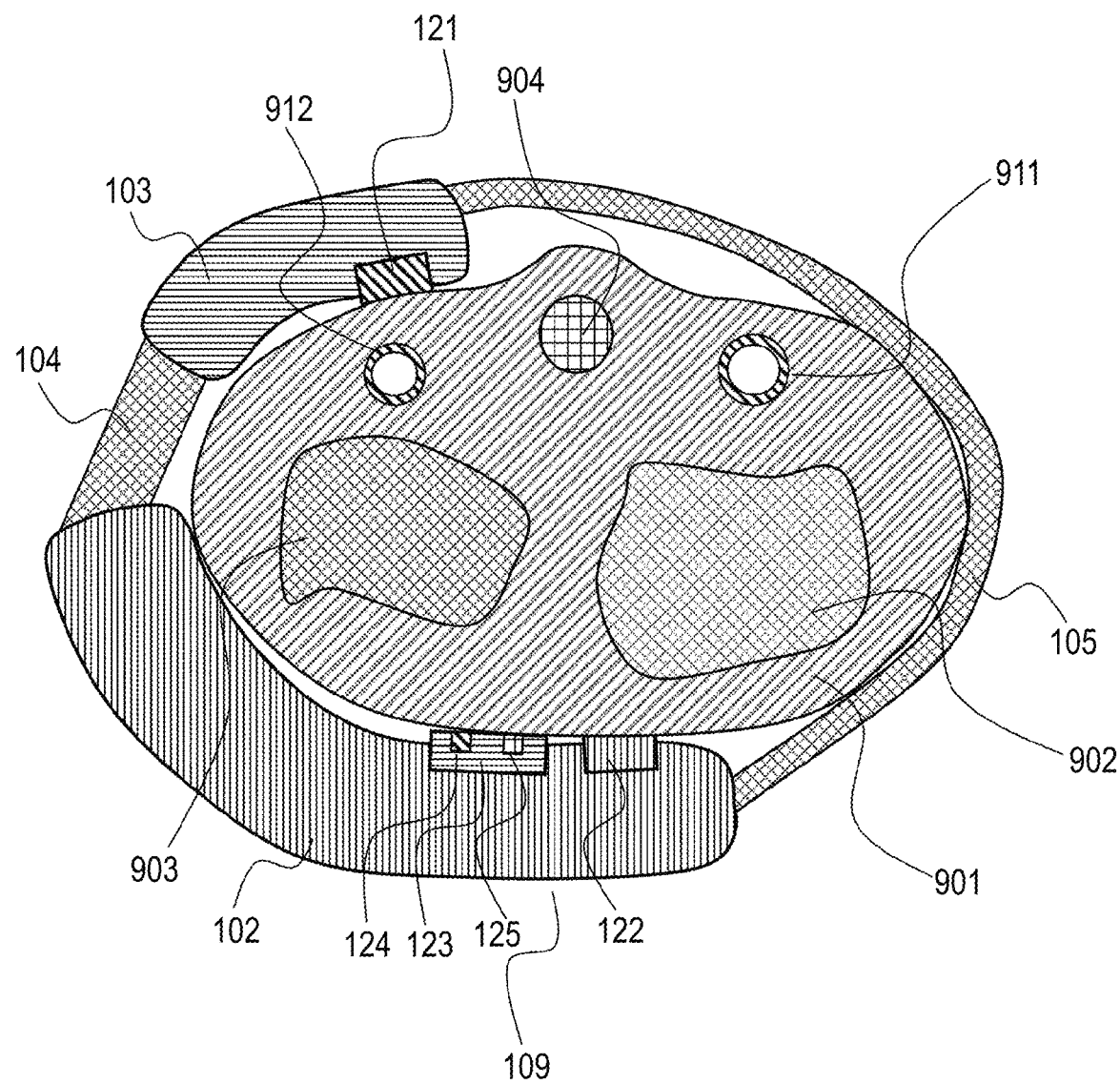
FIG. 13 is a view for explaining the left arm of the subject wearing the blood pressure information measuring device according to the fifth embodiment, and a cross-section taken along a line D-D in FIG. 12A of the blood pressure information measuring device.

The arm which is the measurement site of the subject by a blood pressure information measuring system 5 according to a fifth embodiment of the present invention and a blood pressure information measuring device 109 will be described. FIG. 12A is a state in which the blood pressure information measuring device is mounted on the left arm of the subject. FIG. 12B is a view showing the radial artery and the ulnar artery in the left arm of the subject in the transparent manner, and showing the positional relationship between the radial artery and the electrode of the blood pressure information measuring device. FIG. 12C is a view showing the positional relationship between the arm of the subject, the electrode of the blood pressure information measuring device 109, and an optical sensor module 123. FIG. 13 shows a cross-section taken along a line D-D in FIG. 12A. The clear difference from the blood pressure information measuring system 1 according to the first embodiment is that the first electrode 121 faces the ulnar artery 912 instead of the radial artery 911, and thus orientations of the main unit 102 and the subunit 103 are changed.

As shown in FIG. 12A and FIG. 13, the blood pressure information measuring device 109 includes the main unit 102 and the subunit 103, and one ends of the main unit 102 and the subunit 103 are connected to each other by the link band 104 made of rubber with electrical wiring disposed therein. Further, the other ends of the main unit 102 and the subunit 103 are connected to each other by the rubber support band 105 for fixing the blood pressure information measuring device 109 to the wrist 901. With such a configuration, the link band 104 can be deformed, and the main unit 102 and the subunit 103 can be pulled together by the rubber elasticity of the support band 105. Therefore, the subject can bring the main unit 102 and the subunit 103 into close contact with the wrist 901 of the subject regardless of thickness of the wrist 901. Note that the main unit 102 and the subunit 103 may be configured to communicate wirelessly without being connected by the electrical wiring. Further, the support band 105 may be matched to the diameter of the wrist by means of the buckle and the hole as two bands like the watch belt.

The main unit 102 is configured to include the second electrode 122, the optical sensor module 123, the measuring device control unit 113 and the like. The main unit 102 includes the measuring device control unit 113 and the like described below. The subunit 103 is provided with the first electrode 121.

As shown in FIG. 12B and FIG. 13, the radial artery 911 and the ulnar artery 912 pass through the arm of the subject. As shown in FIG. 13, the wrist 901 has the radius 902 and the ulna 903 passing therethrough, the radial artery 911 passes between the radius 902 and the skin on the surface of the wrist, and the ulnar artery 912 passes between the ulna 903 and the skin on the surface of the wrist. The radial artery 911 and the ulnar artery 912 are branched from the brachial artery 913 in the upper arm. The tendon 904 is between the radial artery 911 and the ulnar artery 912. The tendon 904 may protrude to raise the skin on the surface of the wrist by movement of the wrist 901. Therefore, as shown in FIG. 13, the main unit 102 and the subunit 103 of a blood pressure information measuring device 109 do not easily touch the skin near the tendon 904, which can make it difficult for the subject to feel discomfort in wearing.

The first electrode 121 shown in FIG. 12B and FIG. 13 is disposed near the ulnar artery on the back side of hand of the wrist 901, and detects the potential associated with the electrocardiogram from the ulnar artery. The ulnar artery 912 is branched with the radial artery 911 from the brachial artery 913, and distances from the branch portion is substantially equal near the wrist, so that the electrocardiographic waveform can be obtained also in the ulnar artery. The second electrode 122 shown in FIG. 12C and FIG. 13 is disposed on the palm side of the wrist 901, and detects the living body reference potential. With such a configuration, by measuring the potential detected by the first electrode 121 with the second electrode 122 as the reference potential as time passes, it is possible to obtain the electrocardiogram and measure the electrocardiogram waveform. In addition, since the second electrode 122 can suppress variation of the measured reference potential, it is possible to improve the detection accuracy of the electrocardiogram waveform accompanied by the minute change of the T wave and the like, and to accurately measure the change in the ventricular diastolic phase pulse transit time PTT_DIA.

As shown in FIG. 12C and FIG. 13. the optical sensor module 123 is configured to include the light emitter 124 and the light receiver 125. The light emitter 124 is the light emitting LED having the center wavelength of 660 nm, and the light receiver 125 is formed of the photodiode capable of receiving the light emission wavelength of the light emitting LED. The light emitted from the light emitter 124 to the wrist is reflected inside the wrist and received by the light receiver 125.

<Description of Effects>

As described above, the blood pressure information measuring system 5 according to the fifth embodiment of the present invention detects the electrocardiogram waveform using the ulnar artery 912, so that the subunit 103 can be placed on a little finger side when the subject wears the blood pressure information measuring device 109. Therefore, the blood pressure information measuring system 5 can detect the accurate change related to the blood pressure information even if a position of the subunit 103 is changed depending on wearing preference of the subject.

(Program 1)

Figure 14:
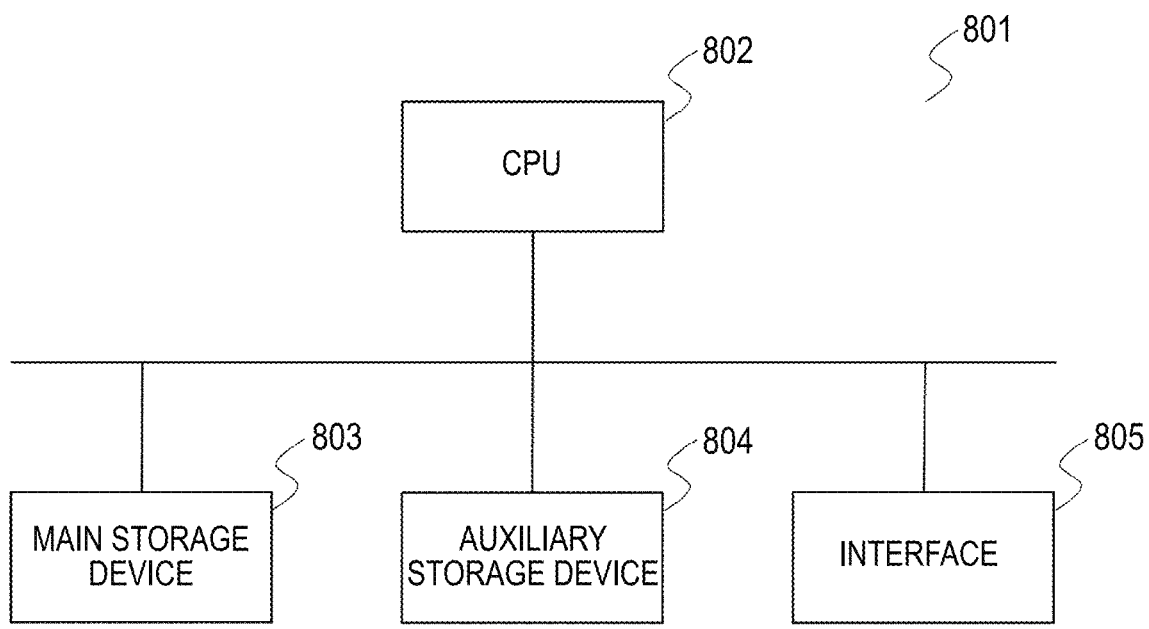
FIG. 14 is a schematic block diagram showing a configuration of a computer according to the embodiments.

FIG. 14 is a schematic block diagram showing a configuration of a computer 801. The computer 801 includes a CPU 802, a main storage device 803, an auxiliary storage device 804, and an interface 805.

Here, details of a program for realizing each function constituting the blood pressure information measuring system 1 according to the first embodiment will be described.

The server device 401 is mounted on the computer 801. An operation of each component of the server device 401 is stored in the auxiliary storage device 804 in a form of program. The CPU 802 reads the program from the auxiliary storage device 804, develops the program in the main storage device 803, and executes the above processing according to the program. Further, the CPU 802 secures a storage area corresponding to the above-described storage unit in the main storage device 803 according to the program.

Specifically, in the computer 801, the program is a computation program for computing the blood pressure information of the subject by the computer, which can be connected to the blood pressure information measuring device having the electrocardiogram detection unit for detecting the electrocardiogram of the subject and the pulse wave detection unit for detecting the pulse wave of the subject. The program is the computation program, in which the computation unit causes the computer to compute the information on the systolic blood pressure of the subject and the information on the diastolic blood pressure of the subject, from the ventricular systolic phase pulse transit time computed from the R wave of the electrocardiogram waveform based on the potential detected by the electrocardiogram detection unit and the P wave of the pulse waveform detected by the pulse wave detection unit, and the ventricular diastolic phase pulse transit time computed from the T wave of the electrocardiogram waveform and the D wave of the pulse waveform.

The auxiliary storage device 804 is an example of a non-transitory tangible medium. Other examples of non-transitory tangible media include magnetic disks, magneto-optical disks, CD-ROMs, DVD-ROMs, semiconductor memories, and the like connected via the interface 805. When the program is distributed to the computer 801 via the network, the distributed computer 801 may develop the program in the main storage device 803 and execute the above processing.

The program may be for realizing a part of the functions described above. Further, the program may be a so-called difference file (difference program) which realizes the above-described functions in combination with other programs already stored in the auxiliary storage device 804.

(Program 2)

Next, details of a program for realizing each function constituting the blood pressure information measuring system 2 according to the second embodiment will be described.

The blood pressure information measuring device 106 is mounted on the computer 801. The operation of each component of the blood pressure information measuring device 106 is stored in the auxiliary storage device 804 in the form of program. The CPU 802 reads the program from the auxiliary storage device 804, develops the program in the main storage device 803, and executes the above processing according to the program. Further, the CPU 802 secures the storage area corresponding to the above-described storage unit in the main storage device 803 according to the program.

Specifically, in the computer 801, the program is a program for measuring the blood pressure information of the subject. The program is the blood pressure information measuring program for causing the computer to perform the following steps: an electrocardiogram detection step of detecting the electrocardiogram of the subject by the electrocardiogram detection unit; a pulse wave detection step of detecting the pulse wave of the subject by the pulse wave detection unit; a first computation step of computing the ventricular systolic phase pulse transit time from the R wave of the electrocardiogram waveform based on the potential detected in the electrocardiogram detection step by the first computation unit and the P wave of the pulse waveform detected in the pulse wave detection step, and the ventricular diastolic phase pulse transit time from the T wave of the electrocardiogram waveform and the D wave of the pulse waveform; and a second computation step of computing the information on the systolic blood pressure of the subject and the information on the diastolic blood pressure of the subject from the ventricular systolic phase pulse transit time and the ventricular diastolic phase pulse transit time which are computed in the first computation step by the second computation unit.

The auxiliary storage device 804 is an example of a non-transitory tangible medium. Other examples of non-transitory tangible media include magnetic disks, magneto-optical disks, CD-ROMs, DVD-ROMs, semiconductor memories, and the like connected via the interface 805.

When the program is distributed to the computer 801 via the network, the distributed computer 801 may develop the program in the main storage device 803 and execute the above processing.

The program may be for realizing a part of the functions described above. Further, the program may be a so-called difference file (difference program) which realizes the above-described functions in combination with other programs already stored in the auxiliary storage device 804.

Although some embodiments of the present invention have been described above, the embodiments can be implemented in other various forms, and various omissions, replacements, and modifications can be made without departing from the gist of the invention. The embodiments and modifications thereof are included in the invention described in claims and the equivalents thereof as well as included in the scope and the gist of the invention.

The invention claimed is:

1. A blood pressure information measuring system for measuring blood pressure information of a subject, comprising:
   an electrocardiogram detector configured to detect an electrocardiogram of the subject;
   a pulse wave detector configured to detect a pulse wave of the subject, wherein the pulse wave detected by the pulse wave detector is a plethysmogram; and
   a processor configured to perform the steps of:
      computing a ventricular systolic phase pulse transit time from an R wave of an electrocardiogram waveform that is a waveform of the electrocardiogram based on a potential detected by the electrocardiogram detector and a P wave of the pulse wave detected by the pulse wave detector, and computing a ventricular diastolic phase pulse transit time from a T wave of the electrocardiogram waveform and a D wave of the pulse wave;
      performing second-order differentiation of the pulse wave to compute an acceleration pulse wave; and
      computing a systolic blood pressure of the subject and a diastolic blood pressure of the subject from the ventricular systolic phase pulse transit time, the ventricular diastolic phase pulse transit time, and characteristic information on the acceleration pulse wave, wherein the processor computes the systolic blood pressure using intensity ratio of an a wave and a b wave of the acceleration pulse wave computed and the ventricular systolic phase pulse transit time, and computes the diastolic blood pressure from intensity ratio of an e wave and an f wave of the acceleration pulse wave computed and the ventricular diastolic phase pulse transit time, and wherein the R wave represents state of ventricular contraction, the P wave is generated by left ventricular ejection, the T wave represents onset of ventricular dilatation, and the D wave is a reflected vibrational wave.

2. The blood pressure information measuring system according to claim 1, wherein the processor is further configured to perform the step comprising:
   computing the systolic blood pressure from the ventricular systolic phase pulse transit time; and
   computing the diastolic blood pressure from the ventricular diastolic phase pulse transit time.

3. The blood pressure information measuring system according to claim 1, wherein the pulse wave detected by the pulse wave detector is a plethysmogram, and the processor is further configured to perform the step comprising:
   computing the systolic blood pressure using intensity of the P wave of the pulse wave; and
   computing the diastolic blood pressure using intensity of the D wave of the pulse wave.

4. The blood pressure information measuring system according to claim 1, wherein the electrocardiogram detector comprises a first electrode and a second electrode.

5. The blood pressure information measuring system according to claim 4, wherein the first electrode and the second electrode are configured to be mounted on a wrist of the subject.

6. The blood pressure information measuring system according to claim 4, wherein the first electrode is configured to be mounted at a position facing the second electrode via a wrist of the subject, and pulse wave detector is configured to be disposed on a palm side of the wrist and is configured to be disposed at a position facing the first electrode via the wrist.

7. The blood pressure information measuring system according to claim 4, wherein the first electrode is configured to be mounted to detect the electrocardiogram of a radial artery of the subject.

8. The blood pressure information measuring system according to claim 4, wherein the first electrode is configured to be mounted to detect the electrocardiogram of an ulnar artery of the subject.

9. The blood pressure information measuring system according to claim 4, wherein the pulse wave detector is disposed near the second electrode.

10. The blood pressure information measuring system according to claim 4, wherein the first electrode is disposed in a first unit, the second electrode and the pulse wave detector are disposed in a second unit, and the first unit and the second unit are movable relative to each other.

11. The blood pressure information measuring system according to claim 1, wherein the pulse wave detector is an optical sensor including a light emitter and a light receiver.

12. The blood pressure information measuring system according to claim 11, wherein the light emitter is a plurality of light emitters having different center light emission wavelength ranges, and
   the blood pressure information measuring system further comprises a controller configured to select and switch the light emitter having a different center emission wavelength range depending on an activity state of the subject.

13. The blood pressure information measuring system according to claim 11, wherein the light emitter is constituted by a first light emitter and a second light emitter, and the light receiver is disposed in an area sandwiched between the first light emitter and the second light emitter.

14. The blood pressure information measuring system according to claim 1, wherein the pulse wave detector is configured to be mounted on a wrist of the subject.

15. A blood pressure information measuring method for measuring blood pressure information of a subject, comprising the following steps:
   an electrocardiogram detection step of detecting an electrocardiogram of the subject by an electrocardiogram detector;
   a pulse wave detection step of detecting a pulse wave of the subject by a pulse wave detector, wherein the pulse wave detected by the pulse wave detector is a plethysmogram;

a first computation step of computing, by a processor, a ventricular systolic phase pulse transit time from an R wave of an electrocardiogram waveform that is a waveform of the electrocardiogram based on a potential detected in the electrocardiogram detection step and a P wave of the pulse wave detected in the pulse wave detection step, and a ventricular diastolic phase pulse transit time from a T wave of the electrocardiogram waveform and a D wave of the pulse wave;

a second computation step of performing, by the processor, second-order differentiation of the pulse wave to compute an acceleration pulse wave; and a third computation step of computing, by the processor, a systolic blood pressure of the subject and a diastolic blood pressure of the subject from the ventricular systolic phase pulse transit time, the ventricular diastolic phase pulse transit time, and characteristic information on the acceleration pulse wave, wherein the processor computes the systolic blood pressure using intensity ratio of an a wave and a b wave of the acceleration pulse wave computed and the ventricular systolic phase pulse transit time, and computes the diastolic blood pressure from intensity ratio of an e wave and an f wave of the acceleration pulse wave computed and the ventricular diastolic phase pulse transit time, and wherein the R wave represents state of ventricular contraction, the P wave is generated by left ventricular ejection, the T wave represents onset of ventricular dilatation, and the D wave is a reflected vibrational wave.

16. A non-transitory computer-readable medium that stores a blood pressure information measuring program for measuring blood pressure information of a subject, the program comprising instructions for:

an electrocardiogram detection step of detecting an electrocardiogram of the subject by an electrocardiogram detector;

a pulse wave detection step of detecting a pulse wave of the subject by the pulse wave detector, wherein the pulse wave detected by the pulse wave detector is a plethysmogram;

a first computation step of computing, by a processor, a ventricular systolic phase pulse transit time from an R wave of an electrocardiogram waveform that is a waveform of the electrocardiogram based on a potential detected in the electrocardiogram detection step and a P wave of the pulse wave detected in the pulse wave detection step, and a ventricular diastolic phase pulse transit time from a T wave of the electrocardiogram waveform and a D wave of the pulse wave;

a second computation step of performing, by the processor, second-order differentiation of the pulse wave to compute an acceleration pulse wave; and a third computation step of computing, by the processor, a systolic blood pressure of the subject and a diastolic blood pressure of the subject from the ventricular systolic phase pulse transit time, the ventricular diastolic phase pulse transit time, and characteristic information on the acceleration pulse wave, wherein the processor computes the systolic blood pressure using intensity ratio of an a wave and a b wave of the acceleration pulse wave computed and the ventricular systolic phase pulse transit time, and computes the diastolic blood pressure from intensity ratio of an e wave and an f wave of the acceleration pulse wave computed and the ventricular diastolic phase pulse transit time, and wherein the R wave represents state of ventricular contraction, the P wave is generated by left ventricular ejection, the T wave represents onset of ventricular dilatation, and the D wave is a reflected vibrational wave.

17. A blood pressure information measuring device for measuring blood pressure information of a subject, comprising:

an electrocardiogram detector configured to detect an electrocardiogram of the subject;

a pulse wave detector configured to detect a pulse wave of the subject, wherein the pulse wave detected by the pulse wave detector is a plethysmogram; and a processor configured to perform the steps of:

computing a ventricular systolic phase pulse transit time from an R wave of an electrocardiogram waveform that is a waveform of the electrocardiogram based on a potential detected by the electrocardiogram detector and a P wave of the pulse wave detected by the pulse wave detector, and computing a ventricular diastolic phase pulse transit time from a T wave of the electrocardiogram waveform and a D wave of the pulse; and performing second-order differentiation of the pulse wave to compute an acceleration pulse wave;

computing a systolic blood pressure of the subject and a diastolic blood pressure of the subject from the ventricular systolic phase pulse transit time, the ventricular diastolic phase pulse transit time, and characteristic information on the acceleration pulse wave, wherein the processor computes the systolic blood pressure using intensity ratio of an a wave and a b wave of the acceleration pulse wave computed and the ventricular systolic phase pulse transit time, and computes the diastolic blood pressure from intensity ratio of an e wave and an f wave of the acceleration pulse wave computed and the ventricular diastolic phase pulse transit time, and wherein the R wave represents state of ventricular contraction, the P wave is generated by left ventricular ejection, the T wave represents onset of ventricular dilatation, and the D wave is a reflected vibrational wave.

18. A server device, configured to be connected to a blood pressure information measuring device having an electrocardiogram detector configured to detect an electrocardiogram of a subject and a pulse wave detector configured to detect a pulse wave of the subject, and computes blood pressure information of the subject, wherein the pulse wave detected by the pulse wave detector is a plethysmogram, the server device comprising:

a processor configured to compute a systolic blood pressure of the subject and a diastolic blood pressure of the subject, from a ventricular systolic phase pulse transit time computed from an R wave of an electrocardiogram waveform that is a waveform of the electrocardiogram based on a potential detected by the electrocardiogram detector and a P wave of the pulse wave detected by the pulse wave detector, a ventricular diastolic phase pulse transit time computed from a T wave of the electrocardiogram waveform and a D wave of the pulse wave, and characteristic information on an acceleration pulse wave computed by performing second-order differentiation of the pulse wave, wherein the processor computes the systolic blood pressure using intensity ratio of an a wave and a b wave of the acceleration pulse wave computed and the ventricular systolic phase pulse transit time, and computes the diastolic blood pressure from intensity ratio of an e wave and an f wave of the acceleration pulse wave computed and the ventricular diastolic phase pulse transit time, and wherein the R wave represents state of ventricular contraction, the P wave is generated by left ventricular ejection, the T wave represents onset of ventricular dilatation, and the D wave is a reflected vibrational wave.

19. A server device, configured to be connected to a blood pressure information measuring device having an electrocardiogram detector configured to detect an electrocardiogram of a subject and a pulse wave detector configured to detect a pulse wave of the subject, and computes blood pressure information of the subject, wherein the pulse wave detected by the pulse wave detector is a plethysmogram, and the server device comprises:
a processor configured to perform the steps of:
computing a ventricular systolic phase pulse transit time from an R wave of an electrocardiogram waveform that is a waveform of the electrocardiogram based on a potential detected by the electrocardiogram detector and a P wave of the pulse wave detected by the pulse wave detector, and computing a ventricular diastolic phase pulse transit time from a T wave of the electrocardiogram waveform and a D wave of the pulse wave; and
computing a systolic blood pressure of the subject and a diastolic blood pressure of the subject from the ventricular systolic phase pulse transit time, the ventricular diastolic phase pulse transit time, and characteristic information on an acceleration pulse wave computed by performing second-order differentiation of the pulse wave, wherein the computer computes the systolic blood pressure using intensity ratio of an a wave and a b wave of the acceleration pulse wave computed and the ventricular systolic phase pulse transit time, and computes the diastolic blood pressure from intensity ratio of an e wave and an f wave of the acceleration pulse wave computed and the ventricular diastolic phase pulse transit time, and wherein the R wave represents state of ventricular contraction, the P wave is generated by left ventricular ejection, the T wave represents onset of ventricular dilatation, and the D wave is a reflected vibrational wave.

20. A computation method for computing blood pressure information of a subject by a server device configured to be connected to a blood pressure information measuring device having an electrocardiogram detector configured to detect an electrocardiogram of the subject and a pulse wave detector configured to detect a pulse wave of the subject, wherein the pulse wave detected by the pulse wave detector is a plethysmogram, the method comprising:
a computation step of computing, by a processor, a systolic blood pressure of the subject and a diastolic blood pressure of the subject, from a ventricular systolic phase pulse transit time computed from an R wave of an electrocardiogram waveform that is a waveform of the electrocardiogram based on a potential detected by the electrocardiogram detector and a P wave of the pulse wave detected by the pulse wave detector, a ventricular diastolic phase pulse transit time computed from a T wave of the electrocardiogram waveform and a D wave of the pulse wave, and characteristic information on an acceleration pulse wave computed by performing second-order differentiation of the pulse wave, wherein the processor computes the systolic blood pressure using intensity ratio of an a wave and a b wave of the acceleration pulse wave computed and the ventricular systolic phase pulse transit time, and computes the diastolic blood pressure from intensity ratio of an e wave and an f wave of the acceleration pulse wave computed and the ventricular diastolic phase pulse transit time, and wherein the R wave represents state of ventricular contraction, the P wave is generated by left ventricular ejection, the T wave represents onset of ventricular dilatation, and the D wave is a reflected vibrational wave.

21. A non-transitory computer-readable medium that stores a computation program for computing blood pressure information of a subject by a computer configured to be connected to a blood pressure information measuring device having an electrocardiogram detector configured to detect an electrocardiogram of the subject and a pulse wave detector configured to detect a pulse wave of the subject, wherein
the pulse wave detected by the pulse wave detector is a plethysmogram,
the program comprising instructions to cause the computer to:
compute a systolic blood pressure of the subject and a diastolic blood pressure of the subject, from a ventricular systolic phase pulse transit time computed from an R wave of an electrocardiogram waveform that is a waveform of the electrocardiogram based on a potential detected by the electrocardiogram detector and a P wave of the pulse wave detected by the pulse wave detector, a ventricular diastolic phase pulse transit time computed from a T wave of the electrocardiogram waveform and a D wave of the pulse wave, and characteristic information on an acceleration pulse wave computed by performing second-order differentiation of the pulse wave, wherein the computer computes the systolic blood pressure using intensity ratio of an a wave and a b wave of the acceleration pulse wave computed and the ventricular systolic phase pulse transit time, and computes the diastolic blood pressure from intensity ratio of an e wave and an f wave of the acceleration pulse wave computed and the ventricular diastolic phase pulse transit time, and wherein the R wave represents state of ventricular contraction, the P wave is generated by left ventricular ejection, the T wave represents onset of ventricular dilatation, and the D wave is a reflected vibrational wave.

* * * * *